United States Patent
Padia et al.

[11] Patent Number: 6,011,052
[45] Date of Patent: Jan. 4, 2000

[54] PYRAZOLONE DERIVATIVES AS MCP-1 ANTAGONISTS

[75] Inventors: Janak Khimchand Padia, Ypsilanti; Bruce David Roth, Plymouth; John Edward Strode, Ann Arbor; Bharat Kalidas Trivedi, Farmington Hills, all of Mich.

[73] Assignee: Warner-Lambert Company, Morris Plains, N.J.

[21] Appl. No.: 08/845,729

[22] Filed: Apr. 25, 1997

Related U.S. Application Data

[60] Provisional application No. 60/016,806, Apr. 30, 1996.
[51] Int. Cl.$^7$ ..................... A61K 31/415; C07D 231/06; C07D 231/14; C07D 231/16
[52] U.S. Cl. .................. 514/407; 548/371.4; 548/371.7; 548/372.1
[58] Field of Search ............................. 548/371.4, 371.7, 548/372.1; 54/407

[56] References Cited

U.S. PATENT DOCUMENTS

| | | | |
|---|---|---|---|
| 2,076,714 | 4/1937 | Freedman | 260/28 |
| 3,190,888 | 6/1965 | Wolf et al. | |

(List continued on next page.)

FOREIGN PATENT DOCUMENTS

| | | |
|---|---|---|
| 3538142 | 3/1987 | European Pat. Off. |
| 0306876 | 3/1989 | European Pat. Off. |

(List continued on next page.)

OTHER PUBLICATIONS

"A Novel Ring Expansion Reaction Of 4–Aminoantipyrines To 5–Amino–4(3H)–Pyrimidinones", T. Ueda et al., Heterocycles, vol. 8, 1977, pp. 263–268.

(List continued on next page.)

*Primary Examiner*—Alan L. Rotman
*Attorney, Agent, or Firm*—Elizabeth M. Anderson

[57] ABSTRACT

Pyrazolone derivatives of Formula I or a pharmaceutically acceptable salt thereof are MCP-1 antagonists and are thus useful in the treatment of inflammatory diseases or conditions, atherosclerosis, restenosis, and immune disorders such as arthritis and transplant rejection

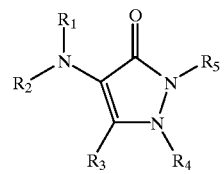

FORMULA I where: $R_1$, $R_2$, $R_3$, $R_4$, $R_5$ can be independently

H, $C_{1-20}$ alkyl, $C_{5-7}$ cycloalkyl,

—$(CH_2)_nNR_6R_7$

—$(CH_2)_{0-6}CONR_6R_7$,

—$(CH_2)_nOH$ or

—$(CH_2)_{0-6}CO_2R_{11}$, biphenyl, aryl of from 6 to 10 carbon atoms, or aryl of from 6 to 10 carbon atoms substituted up to 3 times by halogen, —CN, lower alkyl of from 1–4 carbon atoms, —OH, nitro, —$SO_2H$, $SO_2$ lower alkyl, —$SO_2NR_6R_7$ lower alkoxy

—$CO_2R_{11}$,

—$CONR_6R_7$,

—$NR_6R_7$ or $CH_2OH$.

18 Claims, 3 Drawing Sheets

U.S. PATENT DOCUMENTS

| | | | |
|---|---|---|---|
| 3,244,593 | 4/1966 | Schoen | 514/341 |
| 3,420,839 | 1/1969 | Banci et al. | 546/179 |
| 3,767,400 | 10/1973 | Hayakawa et al. | 430/199 |
| 4,134,987 | 1/1979 | Huppatz | 514/406 |
| 4,537,966 | 8/1985 | Murray et al. | 514/300 |
| 4,654,349 | 3/1987 | Irikura et al. | 514/300 |
| 4,840,879 | 6/1989 | Kamitakahara et al. | 430/406 |
| 4,855,216 | 8/1989 | Mecki et al. | 430/406 |
| 4,877,881 | 10/1989 | Belliotti et al. | 548/240 |
| 4,891,057 | 1/1990 | Sohn et al. | 504/105 |
| 4,924,002 | 5/1990 | Kostlan | 548/206 |
| 4,968,687 | 11/1990 | Findeisen et al. | 514/269 |
| 4,988,718 | 1/1991 | Findeisen et al. | 514/269 |
| 5,006,660 | 4/1991 | Yamakawa | 546/316 |
| 5,108,890 | 4/1992 | Wielinger et al. | 435/4 |
| 5,190,862 | 3/1993 | Wielinger et al. | 435/23 |
| 5,208,251 | 5/1993 | Belliotti et al. | 514/372 |
| 5,227,486 | 7/1993 | Merce-Vidal et al. | 544/295 |
| 5,234,818 | 8/1993 | Zimmermann et al. | 435/28 |
| 5,283,341 | 2/1994 | Tanaka et al. | 548/262.2 |
| 5,463,071 | 10/1995 | Himmelsbach et al. | 548/251 |
| 5,484,708 | 1/1996 | Hoenes et al. | 435/14 |
| 5,510,365 | 4/1996 | Wachtler et al. | 514/407 |
| 5,518,588 | 5/1996 | Fechtel et al. | 205/426 |
| 5,672,617 | 9/1997 | Wachtler et al. | 514/407 |

FOREIGN PATENT DOCUMENTS

| | | |
|---|---|---|
| 0346870 | 12/1989 | European Pat. Off. . |
| 0380897 | 8/1990 | European Pat. Off. . |
| 0423742 | 4/1991 | European Pat. Off. . |
| 0423796 | 4/1991 | European Pat. Off. . |
| 0434413 | 6/1991 | European Pat. Off. . |
| 0442029 | 8/1991 | European Pat. Off. . |
| 0456148 | 11/1991 | European Pat. Off. . |
| 0 511 865 A1 | 11/1992 | European Pat. Off. . |
| 0530011 | 3/1993 | European Pat. Off. . |
| 0534703 | 3/1993 | European Pat. Off. . |
| 0538231 | 4/1993 | European Pat. Off. . |
| 0554834 | 8/1993 | European Pat. Off. . |
| 0600518 | 6/1994 | European Pat. Off. . |
| 0 638 556 A1 | 7/1994 | European Pat. Off. . |
| 0610140 | 8/1994 | European Pat. Off. . |
| 0619374 | 10/1994 | European Pat. Off. . |
| 1470223 | 12/1969 | Germany . |
| 84014 | 8/1971 | Germany . |
| 157704 | 12/1982 | Germany . |
| 4111103 | 6/1941 | Japan . |
| 477385 | 3/1972 | Japan . |
| 4727112 | 7/1972 | Japan . |
| 4736393 | 9/1972 | Japan . |
| 62-234070 | 10/1987 | Japan . |
| 63-185962 | 8/1988 | Japan . |
| 1203336 | 8/1989 | Japan . |
| 1242521 | 9/1989 | Japan . |
| 37927 | 1/1991 | Japan . |
| 3216645 | 9/1991 | Japan . |
| 3227975 | 10/1991 | Japan . |
| 51063 | 1/1993 | Japan . |
| 545789 | 2/1993 | Japan . |
| 5150429 | 6/1993 | Japan . |
| 5163269 | 6/1993 | Japan . |
| 5165161 | 6/1993 | Japan . |
| 616667 | 1/1994 | Japan . |
| 683082 | 3/1994 | Japan . |
| 6199804 | 7/1994 | Japan . |
| 6199805 | 7/1994 | Japan . |
| 6199806 | 7/1994 | Japan . |
| 6345728 | 12/1994 | Japan . |
| 716698 | 1/1995 | Japan . |
| 186492 | 10/1966 | Russian Federation . |
| 477366 | 2/1979 | Spain . |
| 1566696 | 5/1991 | U.S.S.R. . |
| 1662566 | 7/1991 | U.S.S.R. . |
| 1744603 | 6/1992 | U.S.S.R. . |
| 571067 | 4/1993 | U.S.S.R. . |
| 1 455 967 | 11/1976 | United Kingdom . |
| 1 472 052 | 4/1977 | United Kingdom . |
| 8905356 | 6/1989 | WIPO . |
| 9408991 | 4/1994 | WIPO . |
| 9413661 | 6/1994 | WIPO . |
| 9421632 | 9/1994 | WIPO . |
| WO95/19436 | 7/1995 | WIPO . |

OTHER PUBLICATIONS

"Studies On Synthetic Methods for 5–Amino–4(3H)–pyrimidones. I. A Novel Ring Expansion Reaction of 4–Aminoantipyrines to 5–Amino–4(3H)–pyrimidones", T. Ueda et al, Chem Pharm. Bull, 28(7), 2144–2147 (1980).

"Bacterial Degradation Of Aminopyrine", H. Blecher et al., Xenobiotica, 1981, vol. 11, No. 11, 749–754.

"Synthesis and analgesic activity of 4–amino–1, 2–dihydro–5–(2–hydroxyphenyl)–3H–pyrazol–3–ones and 5–amino–6–(2–hydroxyphenyl)pyrimidin–4(3H)–ones", Takagi et al., Eur. J. Med. Chem. 22 (1987), 239–242.

"A Rapid Screening Test To Determine The Antioxidant Potencies Of Natural And Synthetic Antioxidants", W.A. Pryor et al., J. Org. Chem., vol. 58, No. 13, 1993.

"Investigations In Heterocycles. XV. Methylphenidate: A Versatile Intermediate in the Synthesis of Bicyclic Heterocycles with a Bridgehead Nitrogen Atom", G. DeStevens et al., J. Med Chem 7(2) 146–9 (1968).

"Evaluation and Synthesis of Aminohydroxyisoxazoles and Pyrazoles as Potential Glycine Agonists", J. Drummond et al., J. Med. Chem, 1989, 32, pp. 2116–2128.

J. Med. Chem. (1989), 32(9), 2116–28, Journal.

Khim. Geterotsikl. Soedin. (1969), (5), 851–5, Journal, Answer 1 of 2.

Khim. Geterotsikl. Soedin. (1969), (5), 851–5, Journal, Answer 2 of 2.

Ozdowska and Szczycinski, "New derivatives of N–benzyl–4–carbethoxy–3–piperidone. Part I", *Rocz. Chem.*, vol. 50, No. 10, 1976, 1771–1775.

Bosch and Bonjoch, "Synthetic Route to 6–Functionalized 2–Azabicyclo[3.3.1]nonanes", *J. Org. Chem.*, vol. 46, No. 8, 1981, 1538–1543.

Krogsgaard–Larsen and Roldskov–Christiansen, "GABA Agonists. Synthesis and structure–activity studies on analogues of isoguvacine and THIP", *Eur. J. Med. Chem.— Chim. Ther.*, vol. 14, No. 2, 1979, 157–164.

Lykkeberg, "Synthesis of Some Pyrazol–5–ols Related to Muscimol", *Acta Chem. Scand.*, Ser. B, 1978, B32(1), 56–60.

Ram, "Synthetic of Some Piperidone Derivatives", *Indian J. Appl. Chem.*, vol. 33, No. 6, 1970, 370–372.

Fargher and King, "XXXVIII. Additive Compounds of Antipyrylamino–diacetic Acid and its Salts with Neutral Salts", *J. Chem. Soc.*, vol. 119, 1921, 292–298.

Takahashi et al., "Studies on the Synthesis of Antipyretic Analgesics. II. Synthesis of N–Substituted Glycine Dimethylamide Derivatives", *Yakugaku Zasshi*, vol. 80, 1960, 639–646.

deStevens and Bernier, "Investigations in Heterocycles. XV. Methylphenidate: A Versatile Intermediate in the Synthesis of Bicyclic Heterocylces with a Bridgehead Nitrogen Atom", *J. Med. Chem.*, vol. 7, 1964, 146–149.

Mikhlina et al., "The Synthesis of 1,2–Diazabicyclo[3,3,1] Nonane and 1,9–Diazabicyclo[4,3,0]Nonane. IV", *Chemistry of Heterocyclic Compounds*, vol. 5, 1969, 629–631.

Yakhontov and Pronina, "Fischer Cyclization of 6–Substituted Pyrid–2–ylhydrazones of Cyclohexanone", *Chemistry of Heterocyclic Compounds*, vol. 5, 1969, 851–855.

Yakhontov et al., "Effect of the Character of Ring Fusion on the Basicity of Bicyclic Hydrazines", *Chemistry of Heterocyclic Compounds*, vol. 8, 1972, 197–198.

Simonov and Poludnenko, "5,6–Dihydro–4H–imidazo[4,5,1–i,j]quinoline Derivatives III. Substitution Reactions in the 5,6–Dihydro–4H–imidazo[4,5,i,j]quinoline Series", *Chemistry of Heterocyclic Compounds*, vol. 8, 1972, 218–222.

Inhibition of T Cell Recruitment and Cutaneous Delayed–Type Hypersensitive–Induced Inflammation With Antibodies To Monocyte Chemoattracant Protein–1, American Journal of Patholody, vol. 148, No. 3, Mar. 1996.

"Traffic Signals of Lymphocyte Recirculation and Leukocyte Emigration: The Multistep Paradigm", Timothy A. Springer, Cell vol. 76, Jan. 28, 1994, pp. 301–314.

"Pyrimidines. Part 53. Novel Ring Transformation Induced By The Substituent Effect Of The Phenyl Group. Reaction of 5–Bromo–6–Methyl–1–Phenyluracil Derivatives With Amines And Hydrazine To Give Hydantoins And Pyrazolones", Kosaku Hirota et al., J. chem Soc., 1985, pp. 1137–1142.

"The Action Of $\Delta^2$–Oxazolin–5–ones on 1,3,4–Oxadiazolium Salts", G.V. Boyd et al., 1972, pp. 777–779.

"Double Ring–Transformation Of Dracils to Pyrazolones via Hydantoin Ring system", K. Hirota et al, Heterocycles, vol. 19, No. 12, 1982, pp. 2309–2312.

Foster and Hurst, "Pyrazolopyridines. Part II. Preparation of 3–Substituted 2–Aryl–2H–pyrazolo[4,3–b]pyridines. Acid–catalysed Cyclisation of 2–Arylamino–methyl–3–nitropyridines", *J.C.S. Perkin I*, 1973, 319–324.

Sekikawa et al., "Antituberculous Compounds. XXVIII. Synthesis of Pyrazolopyridines", *J. Heterocyclic Chem.*, vol. 10, 1973, 931–932.

Tserng and Bauer, "Degradative Ring Opening of Pyrido and Pyrazino 3–Benzenesulfonyloxyuracils and Their Conversion to Condensed Pyrazolones and Triazolones (1)", *J. Heterocyclic Chem.*, vol. 11, 1974, 163–166.

Ueda et al., "Novel Utilization of Organoselenium Compounds. I. A Facile Transformation of Fused isoselenazoles to Fused Pyridines", *Chem. Pharm. Bull.*, vol. 33, No. 7, 1985, 3065–3067.

Drummond et al., "Evaluation and Synthesis of Aminohydroxyisoxazoles and Pyrazoles as Potential Glycine Agonists", *J. Med. Chem.*, vol. 32, No. 9, 1989, 2116–2128.

Takahashi and Matsuo, "Studies on the Synthesis of Antipyretic Analgesics. I. Synthesis of N–Substituted Alanine Dimethylamide Derivatives", *Yakugaku Zasshi*, vol. 80, 1960, 171–176.

Chattopadhyay and Saha, "An Unexpected Condensation of Oximinoritriles with Benzylhydrazine: a Facile Route to a Substituted 4,5–Diaminopyrazolone", *J. Chem. Research (S)*, 1995, 76–77.

Singh et al., "Transformation of N–acylaminoacetanilides and N–benzoylglycine into 4–(N,N–dimethylaminomethylene)–2–aryl–2–oxazolin–5–ones using Vilsmeier–Haack reagent and their reactions with nucleophiles", *Indian Journal of Chemistry*, vol. 33B, 1994, 1119–1122.

Homani and Mukerjee, "Reactions of 4–heteromethylene– and 4–heterothylidene–2–phenyl–2–oxazolin–5–ones with different nucleophiles and related studies", *Indian Journal of Chemistry*, vol. 31B, 1992, 411–414.

Takagi, et al., "Synthesis and analgesic activity of 4–amino–1, 2–dihydro–5–(2–hydroxyphenyl)–3H–pyrazol–3–ones and 5–amino–6–(2–hydroxyphenyl)pyrimidin–4(3H)–ones", *Eur. J. Med. Chem.*, vol. 22, 1987, 239–242.

Tripathy and Mukerjee, "Reactions of 4–Anilinomethylene–& 4–Ethoxymethylene–2–phenyl–2–oxazolin–5–ones", *Indian Journal of Chemistry*, vol. 25B, 1986, 1059–1060.

Hirota et al., "Pyrimidines. Part 53. Novel Ring Tranformation induced by the Substituent Effect of the Phenyl Group. Reaction of 5–Bromo–6–methyl–1–phenyluracil Derivatives with Amines and Hydrazine to give Hydantoins and Pyrazolones", *J. Chem. Soc. Perkin Trans. I*, 1985, 1137–1142.

Hirota et al., "Double Ring–Transformation of Uracils to Pyrazolones viaHydantoin Ring System", *Heterocycles*, vol. 19, No. 12, 1982, 2309–2312.

Blecher et al., "Bacterial degradation of aminopyrine", *Xenobiotica*, vol. 11, No. 11, 1981, 749–754.

Ueda et al., "Studies on Synthetic Methods for 5–Amino–4(3H)–pyrimidones. I. A Novel Ring Expansion Reaction of 4–Aminoantipyrines to 5–Amino–4(3H)–pyrimidones", *Chem. Pharm. Bull.*, vol. 28, No. 7, 1980, 2144–2147.

Gagliardi et al., "Separation and determination of aminophenazone and methylniphenazine present in combination", *Riv. Tossicol. Sper. Clin.*, vol. 8, Nos. 4–5, 1978, 413–420.

Ueda et al., "A Novel Ring Expansion Reaction of 4–Aminoantipyrines to 5–Amino–4(3H)–pyrimidinones", *Heterocycles*, vol. 8, 1977, 263–268.

Boyd and Dando, "The Action of $^2$–Oxazolin–5–ones on 1,3,4–Oxadiazolium Salts", *J. Chem. Soc. Perkin Trans. I*, vol. 6, 1972, 777–779.

Silli, "Clinical experience of the antipyretic and anagelsic effects of an association of a new pyrazolone (methylniphenazine) and aminopyrine in children", *Miverva Pediat.*, vol. 21, No. 50, 1969, 2364–2372.

J. Chem. Res., Synop. (1995), (2), 76–7,Journal, 1 of 14.

Indian J. Chem., Sect. B: Org. Chem. Incl. Med. Chem (1994), 33B(12), 1119–22, Journal, 2 of 14.

Indian J. chem., Sect. B (1992), 31B(7), 411–14, Journal, 3 of 14.

J. Med. Chem. (1989), 32(9), 2116–28, Journal, 4 of 14.

Eur. J. Med. Chem (1987), 22(3), 239–42, Journal, 5 of 14.

Indian J. chem., Sect. B (1986), 25B (1986), 25B(10), 1059–60, Journal, 6 of 14.

J. chem. Soc., Perkin Trans. 1 (1985), (6), 1137–42, Journal, 7 of 14.

Heterocycles (1982), 19(12), 2309–12, Journal 8 of 14.

Xenobiotica (1981), 11(11), 749–54, Journal, 9 of 14.

Chem. Pharm. Bull. (1980), 28(7), 2144–7, Journal, 10 of 14.

Riv. Tossicol.: Sper. Clin. (1978), 8(4–5), 413–20, Journal, 11 of 14.

Heterocycles (1977), 8, 263–8, Journal, 12 of 14.

J. chem. Soc., Perkin Trans. 1 (1972), (6), 777–9, Journal, 13 of 14.

Minerva Pediat. (1969), 21(50), 2364–72, Journal, 14 of 14.

PYRAZOLONE DERIVATIVES AS MCP-1 ANTAGONISTS

This application claims the benefit of U.S. Provisional Application Ser. No. 60/016,806 filed Apr. 30, 1996.

FIELD OF THE INVENTION

The present invention relates to novel compounds and medical methods of treatment of inflammation, atherosclerosis, restenosis, and immune disorders especially those associated with lymphocyte or monocyte accumulation such as arthritis and transplant rejection. More particularly, the present invention concerns the use of pyrazolone derivatives.

BACKGROUND OF THE INVENTION

Migration of leukocytes from blood vessels into diseased tissues is important to the initiation of normal disease-fighting inflammatory responses. But this process, known as leukocyte recruitment, is also involved in the onset and progression of debilitating and life-threatening inflammatory and autoimmune diseases. The pathology of these diseases results from the attack of the body's immune system defenses on normal tissues. Thus, blocking leukocyte recruitment to target tissues in inflammatory and autoimmune disease would be a highly effective therapeutic intervention. The leukocyte cell classes that participate in cellular immune responses include lymphocytes, monocytes, neutrophils, eosinophils and basophils. In many cases, lymphocytes are the leukocyte class that initiates, coordinates, and maintains chronic inflammatory responses, and thus are generally the most important class of cells to block from entering inflammatory sites. Lymphocytes attract monocytes to the site, which, collectively with lymphocytes, are responsible for such of the actual tissue damage that occurs in inflammatory disease. Infiltration of lymphocytes and/or monocytes is responsible for a wide range of chronic, autoimmune diseases, and also organ transplant rejection. These diseases include, but are not limited to, rheumatoid arthritis, atherosclerosis, psoriasis, chronic contact dermatitis, inflammatory bowel disease, multiple sclerosis, sarcoidosis, idiopathic pulmonary fibrosis, dermatomyositis, skin pemphigoid and related diseases, (e.g., pemphigus vulgaris, p. foliacious, p. erythematosis), glomerulonephritides, vasculitides, hepatitis, diabetes, allograft rejection, and graft-versus-host disease.

This process by which leukocytes leave the bloodstream and accumulate at inflammatory sites, and initiate disease, is best understood for neutrophils and monocytes, but is likely to be similar for other lymphocytes. This process takes place in at least three distinct steps which have been described as (1) rolling, (2) activation/firm adhesion and (3) transendothelial migration [Springer, T. A., Nature 346:425–433 (1990); Lawrence and Springer, Cell 65:859–873 (1991); Butcher, E. C., Cell 67:1033–1036 (1991)]. The second step is mediated at a molecular level by chemoattractant receptors. Chemoattractant receptors on the surface of leukocytes bind chemoattractant cytokines secreted by cells at the site of damage or infection. Receptor binding activates leukocytes, and increases the adhesiveness of the adhesion molecules that mediate transendothelial migration.

A recent discovery is the existence of a large family (>20 members) of structurally homologous chemoattractant cytokines, approximately 8 to 10 kD in size. These moleculles share the ability to stimulate directed cell migration (chemotaxis) and have been collectively called "chemokines", a contraction of chemotactic cytokines. All of these molecules contain four cysteine residues (C) and two internal disulfide bonds. Chemokines can be grouped into two subfamilies, based on whether the two amino terminal cysteine residues are immediately adjacent (C-C family) or separated by one amino acid (C-X-C family). These differences correlate with the organization of the two subfamilies into separate gene clusters. Within each gene cluster, the chemokines typically show sequence similarities between 25 to 60%.

The chemokines of the C-X-C subfamily, such as interleukin-8, are produced by a wide range of cell types and act predominantly on neutrophils as mediators of acute inflammation. Chemokines of the C-C subfamily are also produced by a wide variety of cell types. These molecules act predominantly on subsets of mononuclear inflammatory cells. Currently there are at least six C-C chemokines with known chemotactic activity for human monocytes and/or T cells, including MCP-1, MCP-2, MCP-3, MIP-1-α, MIP-1β and RANTES. This suggests there may be a high degree of redundancy in chemoattractant pathways. In addition, most C-C chemokines are chemotactic for more than one cell type. For examples, RANTES (regulated on activation, normal T cell expressed and secreted) acts on memory $CD4^+T$ cells, eosinophils, and monocytes. Monocytes chemoattractant protein-1 (MCP-1), another C-C chemokine, acts on monocytes, activated "memory" T cells and on basophils. MCP-1 is a potent secretogogue.

Five C-C chemokine receptors have recently been characterized (CKR1-5), and all of these belong to the seven transmembrane spanning G protein-coupled receptor family. Each of these receptors indicates the binding and signalling of more than one chemokine. For example, the CKR1 receptor binds both MIP-1α and RANTES. There are 2 receptors which bind MCP-1, CKR2 (with alternately spliced forms, 2A and 2B) and CKR4. CKR2 is also known to mediate binding and signaling of MCP-3. The CKR4 receptor binds and signals, in addition to MCP-1, with RANTES and MIP-1a. Which of these is responsible for the MCP-1 mediated recruitment of monocytes and T cells is not known.

In agreement with the observation that lymphocyte emigration into inflammatory sites is usually accompanied by emigration of monocytes, MCP-1 is expressed at sites of antigen challenge and autoimmune disease. However, analyses of human inflammatory lesions with antibodies to other chemokines show RANTES, MIP-1α, MIP-1β and MCP-3 to be present as well. Injection of MCP-1 into skin sites in mice provokes only a mild monocyteic infiltrate or no infiltrate at all (Ernst, C. A. et al., J. Immunol. 152:3541–3544, 1994). Whether these results reflect redundant and complex recruitment pathways has not been resolved. MCP-1 and MCP-3 may play a role in allergic hypersensitivity disease. This is also suggested by the observation that MCP-1 lacking the amino terminal glutamic acid loses the ability to stimulate basophil mediator release and acquires activity as an eosinophil chemoattractant.

Chemokines of both subfamilies may bind to heparan sulfate proteoglycans on the endothelial cell surface, and may function principally to stimulate haptotaxis of leukocytes that attach to cytokine-activated endothelium through induced adhesion molecules. Additionally, the MCP-1 chemokine appears to selectively activate the β1 integrin family of leukocyte adhesion molecule, suggesting a role in leukocyte interactions with the extra cellular matrix rather than with the endothelium. Hence, MCP-1 may not only trigger the initial arrest and adhesion of monocytes and T cells, but may rather act to guide their migration in extravascular space.

Chemoattractants appear to be required for transendothelial migration in vitro and in vivo and can induce all steps required for transmigration in vivo. Injection of neutrophil chemoattractants into skin or muscle leads to robust emigration of neutrophils from the vasculature and accumulation at the injection site (Colditz, 1991). Pretreatment of neutrophils with pertussis toxin inhibits emigration into inflammatory sites (Spangrude, et al., 1985; Nourshargh and Williams, 1990). Moreover, MAb to IL-8 markedly inhibits neutrophil emigration in inflammation (Sekido et al., 1993).

Neutrophil chemoattractants injected into the same skin site hours apart will stimulate neutrophil accumulation the first time but not the second time, whereas a second injection into a distant site will stimulate accumulation at that site. This desensitization occurs for homologous chemoattractants only (Colditz, 1991) or those that interact with the same receptor. Thus, chemoattractants can act on and homologously desensitize a cell type that is localized in tissue.

Chemoattractants impart directionality to leukocyte migration. By contrast with intradermal injection, intravascular injection of IL-8 does not lead to emigration (Hechtman et al., 1991). Cytokine-stimulated endothelial monolayers grown on filters secrete IL-8 into the underlying collagen layer. Neutrophils added to the apical compartment emigrate into the basilar compartment, but not when the IL-8 gradient is disrupted by addition of IL-8 to the apical compartment (Huber et al., 1991).

The endothelium may present chemoattractants to leukocytes in a functionally relevant way, as well as providing a permeability barrier that stabilizes the chemoattractant gradient. Since leukocytes, responding to specific antigen or inflammatory signals in tissue, may signal emigration of further leukocytes into the site, a chemoattractant was sought in material secreted by mitogen-stimulated mononuclear cells (Carr et al. 1994). Purification to homogeneity guided by a transendothelial lymphocyte chemotaxis assay revealed that monocyte chemoattractant protein 1 (MCP-1), previously thought to be solely a monocyte chemoattractant, is a major lymphocyte chemoattractant. An activated subset of memory lymphocytes respond to MCP-1. In the same assay, lymphocytes respond to RANTES and MIP-1α but less so than to MCP-1 (C-C chemokines) and not at all to IL-8 or IP-10 (C-X-C chemokines). This physiologically relevant assay suggests that C-C chemokines tend to attract both monocytes and lymphocytes. In agreement with the observation that lymphocyte emigration into inflammatory sites is accompanied by emigration of monocytes, MCP-1 is abundantly expressed at sites of antigen challenge and autoimmune disease (Miller and Kragel, 1992) and, together with other chemokines, is an excellent candidate to provide the step 2 signal required to activate integrin adhesiveness and emigration of lymphocytes in vivo. Traffic Signals for Lymphocyte Recirculation and Leukocyte Emigration: The Multistep Paradigm; Springer, 1994, *Cell* 76: 301–314).

We have surprisingly found that pyrazolone derivates are MCP-1 receptor antagonists (inhibiting the binding of MCP-1 to its receptor). Surprisingly, the compounds block T cell migration in vitro, and more surprisingly still, have dramatic effects on the recruitment of inflammatory cells in multiple models of inflammatory diseases. Thus, these compounds are useful as agents for the treatment of inflammatory disease, especially those associated with lymphocyte or monocyte accumulation or recruitment, such as arthritis, atherosclerosis and transplant rejection. In addition, these compounds can be used in the treatment of allergic hypersensitivity disorders such as asthma and allergic rhinitis characterized by basophil activation and eosinophil recruitment, as well as for the treatment of restenosis and chronic or acute immune disorders.

SUMMARY OF THE INVENTION

Figure 1:
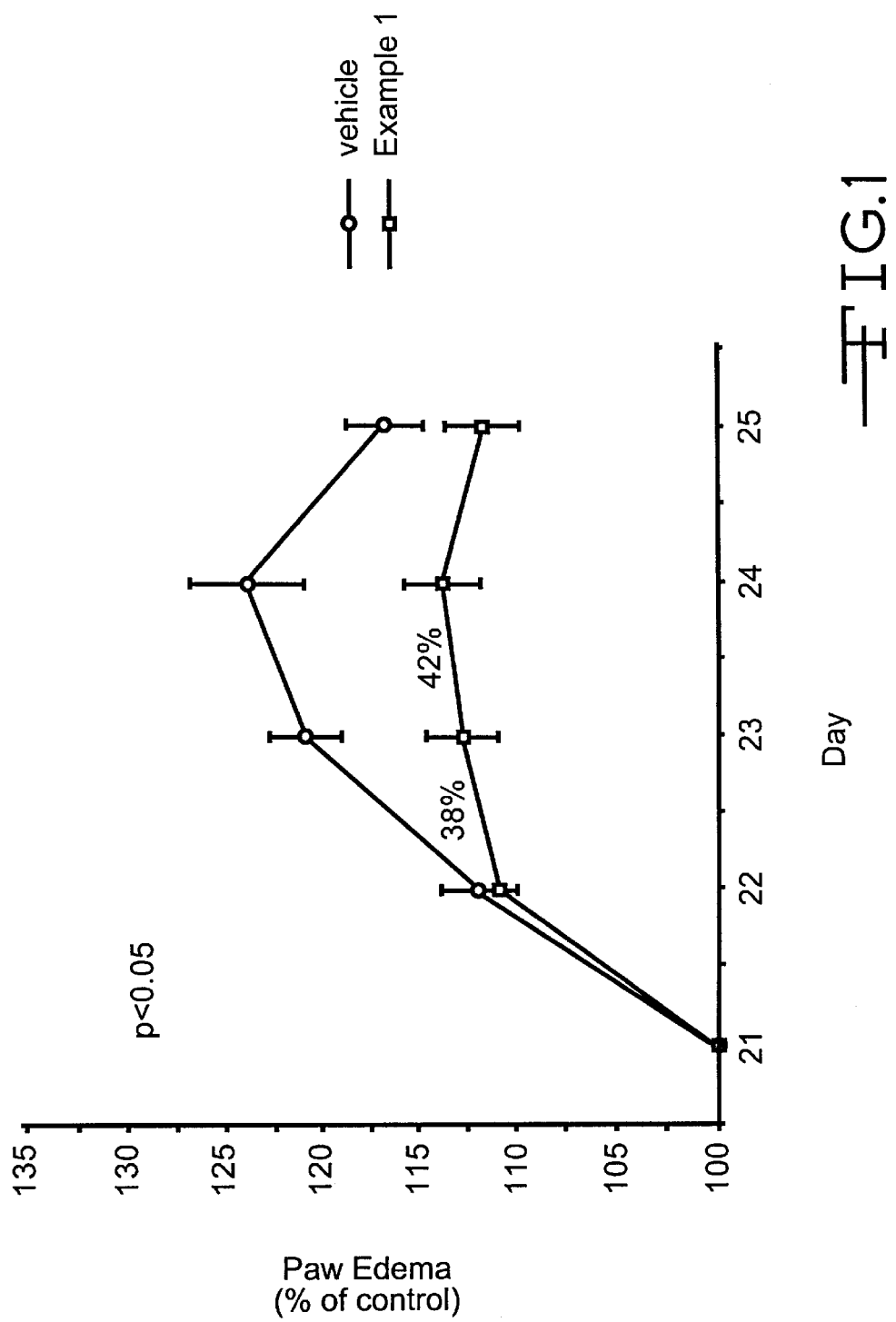
FIGS. 1 and 2 plot the time delay affect of MCP-1 receptor antagonists on streptococcal cell wall (SCW) arthritis induced hind paw edema.

Accordingly, a first embodiment of the present invention provides a method of treatment of chronic or acute inflammatory disease, atherosclerosis, restenosis, chronic or acute immune disorders, and transplant rejection in mammals in need thereof comprising administering to such mammal an effective amount of a pyrazolone of Formula I or a pharmaceutically acceptable salt thereof:

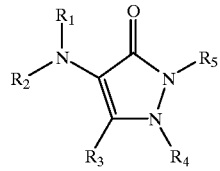

FORMULA I where: $R_1$, $R_2$, $R_3$, $R_4$, $R_5$ can be independently
H,
$C_{1-20}$ alkyl,
$C_{5-7}$ cycloalkyl,
—$(CH_2)_n NR_6 R_7$
—$(CH_2)_{0-6} CONR_6 R_7$,
—$(CH_2)_n OH$,
—$(CH_2)_{0-6} CO_2 R_{11}$,
biphenyl,
aryl of from 6 to 10 carbon atoms, or
aryl substituted up to 3 times by halogen, —CN, lower alkyl of from 1–4 carbon atoms, —OH, nitro, —$SO_2H$, $SO_2$ lower alkyl, —$SO_2NR_6R_7$, lower alkoxy
—$CO_2R_{11}$,
—$CONR_6R_7$,
—$NR_6R_7$ or
—$CH_2OH$;
wherein n is an integer from 0–6 providing n is not 1 when the moiety is $R_1$, $R_2$, $R_4$ and/or $R_5$ and n can not be 0 when the moiety is $R_4$ or $R_5$,
$R_6$ and $R_7$ can be independently
H, lower alkyl of from 1–4 carbon atoms, or
$(CH_2)_n NR_8 R_9$;
$R_8$ and $R_9$ can independently be H, lower alkyl or can be taken together to form a ring of 3–7 atoms containing 0–1 additional heteroatoms as oxygen or sulfur or N—$R_{10}$;
$R_{10}$ is H, alkyl of from 1–4 carbon atoms, $(CH_2)_n Ph$, or $(CH_2)_n CHPh_2$ where "Ph" means phenyl;
$R_6$ and $R_7$ can also be taken together to form a ring of 3–7 atoms containing 0–1 heteroatoms as oxygen or N—$R_{10}$ where $R_{10}$ is as defined above;
$R_{11}$ is H or lower alkyl of from 1–4 carbon atoms;
$R_2$ and $R_3$ or $R_3$ and $R_4$ or $R_4$ and $R_5$ can independently be taken together to form a ring of 5–7 atoms;
further either one of $R_1$ or $R_2$ can independently be —$C(O)R_{12}$, —C(S)R$_{12}$, or
—CO$_2$R$_{12}$,
where R$_{12}$ is lower alkyl of from 1–4 carbon atoms, phenyl or phenyl substituted up to 3 times with substitutents as previously defined above;

R$_3$, R$_4$ and R$_5$ can be independently a 5 or 6 membered aromatic or non-aromatic mono or poly heterocycle containing 1–4 N, O or S atoms with the ring carbon atoms substituted as the phenyl substitutents described above and the non-aromatic nitrogen atoms may be substituted by R$_{10}$.

A still further and second embodiment of the present invention is a method of treatment of atherosclerosis in mammals in need thereof comprising administering to such mammal an effective amount of a compound selected from the group consisting of: pyrazolone of formula I in combination with one or more agents selected from the group consisting of:

(a) ACAT inhibitor;

(b) HMG-CoA reductase inhibitor;

(c) Lipid regulator; and (d) Bile acid sequestrant;

or a pharmaceutically-acceptable salt thereof.

Also, the invention is directed to inhibiting the binding of MCP-1 by utilizing an effective inhibiting amount of a compound of Formula I.

Also, the invention is directed to the novel compositions of Formula I.

Finally, the present invention is directed to a pharmaceutical composition for administering an effective amount of a compound of Formula I in unit dosage form in the treatment methods mentioned above.

DETAILED DESCRIPTION OF THE INVENTION

In the compounds of Formula I, the term "lower alkyl" means a straight or branched hydrocarbon radical having from 1 to 4 carbon atoms and includes, for example, methyl, ethyl, n-propyl, isopropyl, n-butyl, sec-butyl, isobutyl and tert-butyl.

The term "lower alkoxyl" is O-alkyl as defined above for alkyl.

"Halogen" is fluorine, chlorine, bromine, or iodine.

"Aryl" could be phenyl or naphthyl.

"Heterocycle" is defined as a five or six-membered mono or bicyclic ring structure which may contain one or more heteroatoms such as N, O or S; examples of heterocycle are pyridine, thiophene, pyrimidine, pyridazine, pyrazole, thiazole, oxazole, indole, N-alkylindole, quinoline, quinazoline, quinazolinone and the like. Substitutents can be hydrogen, alkyl of from 1–4 carbon atoms; cycloalkyl of from 5–7 carbon atoms, O Alkyl, S Alkyl, (CH$_2$)$_n$—NR$_6$R$_7$, —COOR$_1$, —CH$_2$OR$_1$, —CONR$_6$R$_7$, —COR$_1$, —CH$_2$CONR$_6$R$_7$, SO$_2$NR$_6$R$_7$, NHCOR$_1$, NR$_1$ CONR$_2$ where R$_1$, R$_2$, R$_6$ and R$_7$ are as defined above for Formula I; —CN or halogen.

The term "mammal" includes animals and humans.

Some of the compounds of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *J. Pharma. Sci.*, 1977;66:1).

The acid addition salts of said basic compounds can be prepared by contacting the free base form with a sufficient amount of the desired acid to produce the salt in the conventional manner. The free base form may be regenerated by contacting the salt form with a base and isolating the free base in the conventional manner. The free base forms may differ from their respective salt forms somewhat in certain physical properties such as solubility in polar solvents, but otherwise the salts are equivalent to their respective free base for purposes of the present invention.

Pharmaceutically acceptable base addition salts can be formed with metals or amines, such as alkali and alkaline earth metals or organic amines. Examples of such metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see Berge, Supra, 1977).

The base addition salts of said acidic compounds can be prepared by contacting the free acid form with a sufficient amount of the desired base to produce the salt in the conventional manner. The free acid form may be regenerated by contacting the salt form with an acid and isolating the free acid in the conventional manner. The free acid forms may differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

A preferred compound of the first embodiment used in the method of the present invention is a compound formula I of:

FORMULA I

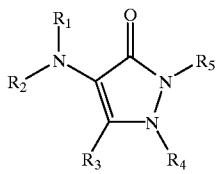

where: $R_1$, $R_2$, $R_3$, $R_4$, $R_5$ can be independently

H, $C_{1-4}$ alkyl, $C_{5-7}$ cycloalkyl,

—$(CH_2)_n NR_6 R_7$

—$(CH_2)_{0-6} CONR_6 R_7$,

—$(CH_2)_n OH$,

—$(CH_2)_{0-6} CO_2 R_{11}$, phenyl, or phenyl substituted up to 3 times by halogen, —CN, lower alkyl of from 1–4 carbon atoms, —OH, nitro, —$SO_2 H$, $SO_2$ lower alkyl, —$SO_2 NR_6 R_7$, lower alkoxy

—$CO_2 R_{11}$,

—$CONR_6 R_7$,

—$NR_6 R_7$ or

—$CH_2 OH$;

wherein n is an integer from 0–6 providing n is not 1 when the moiety is $R_1$, $R_2$, $R_4$ and/or $R_5$ and n can not be 0 when the moiety is $R_4$ or $R_5$;

$R_6$ and $R_7$ can be independently

H, lower alkyl of from 1–4 carbon atoms, or $(CH_2)_n NR_8 R_9$;

$R_8$ and $R_9$ can independently be H, lower alkyl or can be taken together to form a ring of 3–7 atoms containing 0–1 additional heteroatoms as oxygen or sulfur or N—$R_{10}$;

$R_{10}$ is H, alkyl of from 1–4 carbon atoms, $(CH_2)_n Ph$, or $(CH_2)_n CHPh_2$;

$R_6$ and $R_7$ can also be taken together to form a ring of 3–7 atoms containing 0–1 heteroatoms as oxygen or N—$R_{10}$ where $R_{10}$ is as defined above;

$R_{11}$ is H or lower alkyl of from 1–4 carbon atoms;

$R_2$ and $R_3$ or $R_3$ and $R_4$ or $R_4$ and $R_5$ can independently be taken together to form a ring of 5–7 atoms;

further either one of $R_1$ or $R_2$ can independently be

—$C(O)R_{12}$,

—$C(S)R_{12}$, or

—$CO_2 R_{12}$, where $R_{12}$ is lower alkyl of from 1–4 carbon atoms, phenyl or phenyl substituted up to 3 times with substitutents as previously defined above;

$R_3$, $R_4$ and R. can be independently a 5 or 6 membered aromatic or non-aromatic mono or poly heterocycle containing 1–4 N, O or S atoms with the ring carbon atoms substituted as the phenyl substitutents described above and the non-aromatic nitrogen atoms may be substituted by $R_{10}$ or a pharmaceutically acceptable salt of a compound of Formula I.

Examples of fused ring pyrazoles are as follows:

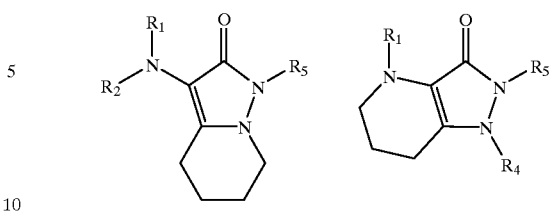

where $R_1$, $R_2$, $R_4$ and $R_5$ are as above.

A pyrazolone compound can be administered to a mammal (e.g., a human) alone or in conjunction with (before, along with or subsequent to) one or more other pyrazolone compounds or another agent to be administered. Preferred compounds used in the second embodiment of the present invention include one or more agents selected from the group consisting of an acyl CoA:cholesterol acyltransferase (ACAT) inhibitor; 3-hydroxy-3-methylglutaryl-coenzyme A reductase (HMG-COA reductase) inhibitor; lipid regulator; and bile acid sequestrant.

Examples of ACAT inhibitors include DL-melinamide disclosed in British Patent 1,123,004 and Japan. J. Pharmacol., 1986;42:517–523; 2,2-dimethyl-N-(2,4,6-trimethoxyphenyl)dodecanamide disclosed in U.S. Pat. No. 4,716,175; N-[2,6-bis(1-methylethyl)phenyl]-N'-[[1-(4-dimethylaminophenyl)cyclopentyl]methyl]urea disclosed in U.S. Pat. No. 5,015,644; 2,6-bis(1-methyl-ethyl)phenyl[[2,4,6-tris(1-methylethyl)phenyl]-acetyl]sulfamate disclosed in copending U.S. patent application Ser. No. 08/233,932 filed Apr. 13, 1994; and the like. U.S. Pat. Nos. 4,716,175 and 5,015,644 and U.S. patent application Ser. No. 08/233, 932 and British Patent 1,123,004 and Japan. J. Pharmacol., 1986;42:517–523 are hereby incorporated by reference.

Examples of HMG-CoA reductase inhibitors include lovastatin disclosed in U.S. Pat. No. 4,231,938; pravastatin disclosed in U.S. Pat. No. 4,346,227; simvastatin disclosed in U.S. Pat. No. 4,444,784; fluvastatin disclosed in U.S. Pat. No. 4,739,073; atorvastatin disclosed in U.S. Pat. Nos. 4,681,893 and 5,273,995; and the like. U.S. Pat. Nos. 4,231,938; 4,346,227; 4,444,784; 4,681,893; 4,739,073 and 5,273,995 are hereby incorporated by reference.

Examples of bile acid sequestrants include colestipol disclosed in U.S. Pat. Nos. 3,692,895 and 3,803,237; cholestyramine disclosed in U.S. Pat. No. 3,383,281 and Casdorph R. in Lipid Pharmacology., 1976;2:222–256, Paoletti C., Glueck J., eds. Academic Press, NY; and the like. U.S. Pat. Nos. 3,692,895; 3,803,237 and 3,383,281 and R. Casdorph, supra, 1976, are hereby incorporated by reference.

Examples of lipid regulators include gemfibrozil described in U.S. Pat. No. 3,674,836; bezafibrate disclosed in U.S. Pat. No. 3,781,328; clofibrate disclosed in U.S. Pat. No. 3,262,850; fenofibrate disclosed in U.S. Pat. No. 4,058,552; niacin disclosed in McElvain, et al., Org. Syn., 1925;4:49; and the like. U.S. Pat. Nos. 3,674,836; 3,781, 328; 3,262,850 and 4,058,552 and McElvain, et al., Org. Syn., 1925;4:49 are hereby incorporated by reference.

Methods of preparing ACAT inhibitors, HMG-COA reductase inhibitors, lipid regulators, and bile acid sequestrants used in the second embodiment of the present invention are disclosed in the aforementioned references.

The invention is also concerned with novel compounds as pyrazolone derivaties:

A compound of formula I

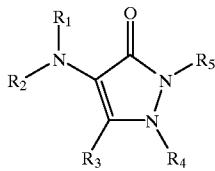

FORMULA I where: $R_1$ and $R_2$ can independently be
—$(CH_2)_n NR_8 R_9$;
$R_3$, $R_4$, and $R_5$ can be independently
H,
$C_{1-20}$ alky,
$C_{5-7}$ cycloalkyl,
—$(CH_2)_n NR_6 R_7$,
—$(CH_2)_{0-6} CONR_6 R_7$,
—$(CH_2)_n OH$,
—$(CH_2)_{0-6} CO_2 R_{11}$,
biphenyl,
phenyl, or
phenyl substituted up to 3 times by halogen,
 —CN, lower alkyl of from 1–4 carbon atoms, —OH,
 nitro,
 —$SO_2 H$,
 —$SO_2$ lower alkyl,
 —$SO_2 NR_6 R_7$
 lower alkoxy
 —$CO_2 R_{11}$,
 —$CONR_6 R_7$,
 —$NR_6 R_7$ or
 —$CH_2 OH$;
where n is an integer from 0–6; providing that n is not 1 when the moiety is $R_1$, $R_2$, $R_4$ and/or $R_5$ and n can not be 0 when the moiety is $R_4$ or $R_5$;
$R_6$ and $R_7$ can be independently
H, lower alkyl of from 1–4 carbon atoms, or
$(CH_2)_n NR_8 R_9$;
$R_8$ and $R_9$ can be independently H, lower alkyl or can be taken together to form a ring of 3–7 atoms containing 0–1 additional heteroatoms as oxygen or sulfur or N—$R_{10}$;
$R_{10}$ is H, alkyl of from 1–4 carbon atoms, $(CH_2)_n Ph$, or $(CH_2)_n CHPh_2$;
$R_6$ and $R_7$ can also be taken together to form a ring of 3–7 atoms containing 0–1 heteroatoms as oxygen or N—$R_{10}$ where $R_{10}$ is as defined above;
$R_{11}$ is H or lower alkyl of from 1–4 carbon atoms;
$R_2$ and $R_3$ or $R_3$ and $R_4$ or $R_4$ and $R_5$ can independently be taken together to form a ring of 5–7 atoms;
$R_3$, $R_4$ and $R_5$ can be independently a 5 or 6 membered aromatic or non-aromatic mono or poly heterocycle containing 1–4 N, O or S atoms with the ring carbon atoms substituted as the phenyl substitutents described above and the non-aromatic nitrogen atoms may be substituted by $R_{10}$.

A compound of Formula I

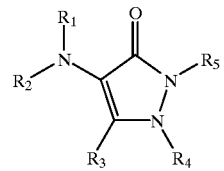

FORMULA I where: $R_1$, $R_4$, and $R_5$ can be independently
H,
$C_{1-20}$ alkyl,
$C_{5-7}$ cycloalkyl,
—$(CH_2)_n NR_6 R_7$,
—$(CH_2)_{0-6} CONR_6 R_7$,
$(CH_2)_n OH$,
—$(CH_2)_{0-6} CO_2 R_{11}$,
biphenyl,
aryl of from 6 to 10 carbon atoms, or
aryl of from 6 to 10 carbon atoms substituted up to 3 times
 by halogen, —CN, lower alkyl of from 1–4 carbon atoms,
 —OH, nitro, —$SO_2 H$, $SO_2$ lower alkyl,
 —$SO_2 NR_6 R_7$, lower alkoxy
 —$CO_2 R_{11}$,
 —$CONR_6 R_7$,
 —$NR_6 R_7$ or
 —$CH_2 OH$;
wherein n is an integer from 0–6, providing n is not 1 when the moiety is $R_1$, $R_2$, $R_4$ and/or $R_5$ and n can not be 0 when the moiety is $R_4$ or $R_5$;
$R_2$ and $R_3$ are taken together to form a ring of 5–7 atoms (containing carbon, O, N and/or sulfur);
$R_6$ and $R_7$ can be independently
H, lower alkyl of from 1–4 carbon atoms, or
$(CH_2)_n NR_8 R_9$;
$R_8$ and $R_9$ can be independently be H, lower alkyl or can be taken together to form a ring of 3–7 atoms containing 0–1 additional heteroatoms as oxygen or sulfur or N—$R_{10}$;
$R_{10}$ is H, alkyl of from 1–4 carbon atoms, $(CH_2)_n Ph$, or $(CH_2)_n CHPh_2$ where "Ph" is phenyl;
$R_6$ and $R_7$ can also be taken together to form a ring of 3–7 atoms containing 0–1 heteroatoms as oxygen or N—$R_{10}$ where $R_{10}$ is as defined above;
$R_{11}$ is H or lower alkyl of from 1–4 carbon atoms;
$R_4$ and $R_5$ may be taken together to form a ring of 5–7 atoms;
further $R_1$ may be
—$C(O)R_{12}$,
—$C(S)R_{12}$, or
—$CO_2 R_{12}$,
where $R_{12}$ is lower alkyl of from 1-4 carbon atoms, phenyl or phenyl substituted up to 3 times with substitutents as previously defined above;
$R_3$, $R_4$ and $R_5$ can also be independently a 5 or 6 membered aromatic or non-aromatic heterocycle containing 1–4 N, O or S atoms with the ring carbon atoms substituted as the phenyl substitutents described above and the non-aromatic nitrogen atoms may be substituted by $R_{10}$.

A compound of Formula I

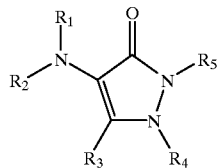

FORMULA I where: $R_1$, $R_2$, and $R_5$ can independently be
H,
$C_{1-20}$ alkyl,
$C_{5-7}$ cycloalkyl,
—$(CH_2)_n NR_6 R_7$,
—$(CH_2)_n CONR_6 R_7$,
—$(CH_2)_n OH$,
—$(CH_2)_n CO_2 R_{11}$,
biphenyl,
aryl of from 6 to 10 carbon atoms, or
aryl of from 6 to 10 carbon atoms substituted up to 3 times by halogen, —CN, lower alkyl of from 1–4 carbon atoms, —OH, nitro, —$SO_2H$,
—$SO_2$ lower alkyl,
—$SO_2 NR_6 R_7$
lower alkoxy
—$CO_2 R_{11}$,
—$CONR_6 R_7$,
—$NR_6 R_7$ or
—$CH_2 OH$;
where n is an integer from 0–6; providing that n is not 1 when the moiety is $R_1$, $R_2$ and/or $R_5$ and n can not be 0 when the moiety is $R_4$ or $R_5$;
$R_3$ and $R_4$ are taken together to form a ring of from 5 to 7 atoms;
$R_6$ and $R_7$ can be independently
H, lower alkyl of from 1–4 carbon atoms, or
$(CH_2)_n NR_8 R_9$;
$R_8$ and $R_9$ can be independently H, lower alkyl or can be taken together to form a ring of 3–7 atoms containing 0–1 additional heteroatoms as oxygen or sulfur or N—$R_{10}$;
$R_{10}$ is H, alkyl of from 1–4 carbon atoms, $(CH_2)_n Ph$, or $(CH_2) CHPh_2$;
$R_6$ and $R_7$ can also be taken together to form a ring of 3–7 atoms containing 0–1 heteroatoms as oxygen or N—$R_{10}$ where $R_{10}$ is as defined above;
$R_{11}$ is H or lower alkyl of from 1–4 carbon atoms;
further either one of $R_1$ or $R_2$ can independently be
—$C(O)R_{12}$,
—$C(S)R_{12}$, or
—$CO_2 R_{12}$,
where $R_{12}$ is lower alkyl of from 1–4 carbon atoms, phenyl or phenyl substituted up to 3 times with substitutents as previously defined above;
$R_3$ and $R_4$ may be a 5 or 6 membered aromatic or non-aromatic heterocycle containing 1–4 N, O or S atoms with the ring carbon atoms substituted as the phenyl substitutents described above and the non-aromatic nitrogen atoms may be substituted by $R_{10}$.

A compound of Formula I

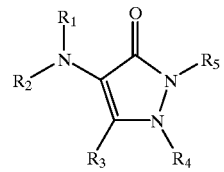

FORMULA I where: $R_1$, $R_2$, $R_4$, $R_5$ can be independently
H,
$C_{1-20}$ alkyl,
$C_{5-7}$ cycloalkyl,
—$(CH_2)_n NR_6 R_7$,
—$(CH_2)_{0-6} CONR_6 R_7$,
—$(CH_2)_n OH$,
—$(CH_2)_{0-6} CO_2 R_{11}$,
biphenyl,
aryl of from 6 to 10 carbon atoms, or
aryl of from 6 to 10 carbon atoms substituted up to 3 times by halogen, —CN, lower alkyl of from 1–4 carbon atoms, —OH, nitro, —$SO_2 H$,
$SO_2$ lower alkyl,
—$SO_2 NR_6 R_7$,
lower alkoxy
—$CO_2 R_{11}$,
—$CONR_6 R_7$,
—$NR_6 R_7$ or
—$CH_2 OH$;
wherein n is an integer from 0–6; providing that n is not 1 when the moiety is $R_1$, $R_2$, $R_4$ and/or $R_5$ and n can not be 0 when the moiety is $R_4$ or $R_5$;
$R_3$ is —$C(O)NH(CH_2)_n NR_6 R_7$;
$R_6$ and $R_7$ can be independently
H, lower alkyl of from 1–4 carbon atoms, or
$(CH_2)_n NR_8 R_9$;
$R_8$ and $R_9$ can independently be H, lower alkyl or can be taken together to form a ring of 3–7 atoms containing 0–1 additional heteroatoms as oxygen or sulfur or N—$R_{10}$;
$R_{10}$ is H, alkyl of from 1–4 carbon atoms, $(CH_2)_n Ph$, or $(CH_2)_n CHPh_2$;
$R_6$ and $R_7$ can also be taken together to form a ring of 3–7 atoms containing 0–1 heteroatoms as oxygen or N—$R_{10}$ where $R_{10}$ is as defined above;
$R_{11}$ is H or lower alkyl of from 1–4 carbon atoms;
$R_4$ and $R_5$ can independently be taken together to form a ring of 5–7 atoms;
further either one of $R_1$ or $R_2$ can independently be
—$C(O)R_{12}$,
—$C(S)R_{12}$, or
—$CO_2 R_{12}$,
where $R_{12}$ is lower alkyl of from 1–4 carbon atoms, phenyl or phenyl substituted up to 3 times with substitutents as previously defined above;
$R_4$ and $R_5$ can be independently a 5 or 6 membered aromatic or non-aromatic heterocycle containing 1–4 N, O or S atoms with the ring carbon atoms substituted as the phenyl substitutents described above and the non-aromatic nitrogen atoms may be substituted by $R_{10}$.

General Synthesis:

Compounds of Formula I can be synthesized as follows, see J. Med. Chem. 1989, Vol. 32:2116–2128:

SCHEME A
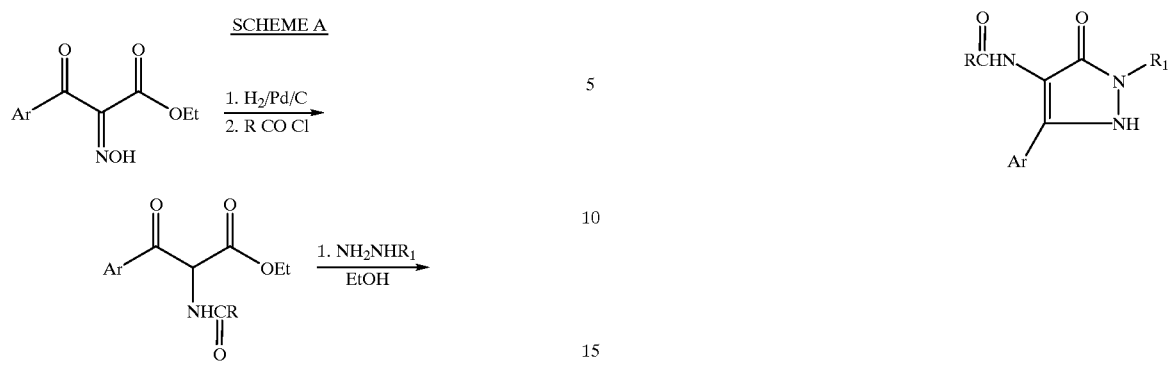
SCHEME B
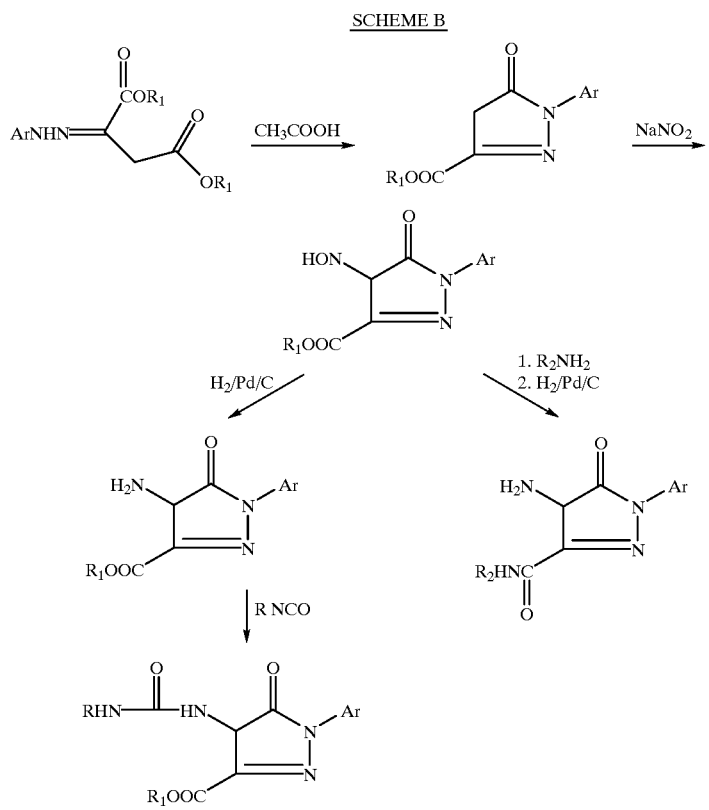
SCHEME C
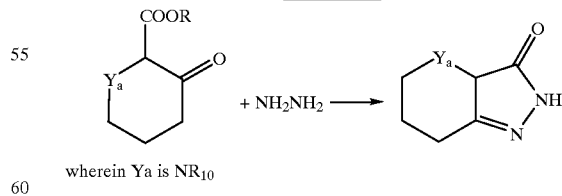
wherein Ya is $NR_{10}$

SCHEME D

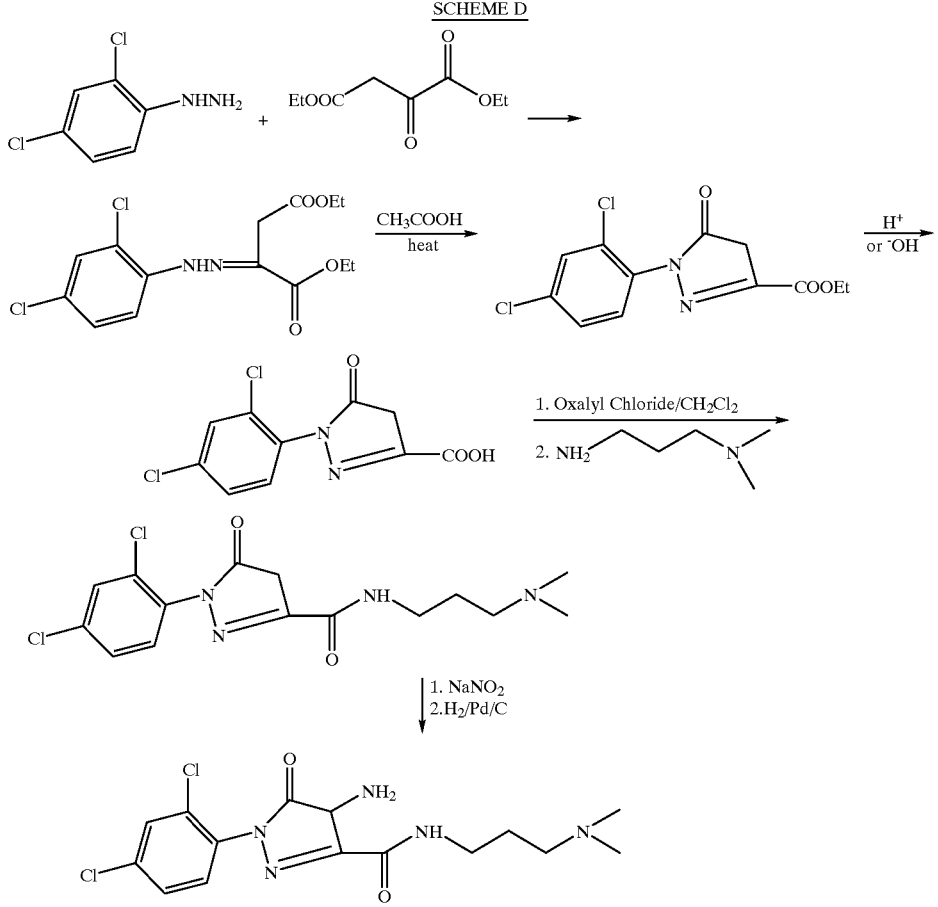

The pyrazolones are valuable agents for the treatment of inflammatory diseases or conditions, atherosclerosis, restenosis, and auto immune disorders such as arthritis and transplant rejection.

In a preferred embodiment, the disease or condition is one which is associated with lymphocyte and/or mnonocyte infiltraion of tissues (including recruitment and/or accumulation in tissues), such as arthritis (e.g., rheumatoid arthritis), inflammatory bowel diseases (e.g., Crohn's disease, ulcerative colitis), multiple sclerosis, idiopathic pulmonary fibrosis, and graft rejection (e.g., in transplantation), including allograft rejection or graft-versus-host disease. In addition, diseases characterized by basophil activation and/or eosinophil recruitment, including allergic hypersensitivity disorders such as asthma and allergic rhinitis can be treated according to the present invention.

Other diseases that may be treated with the pyrazolones of Formula I are:

psoriasis, chronic contact dermatitis, sarcoidosis, dermatonyositis, skin phenphigoid and related diseases (e.g., pemphigus vulgaris, p. foliacious, p. arythhematosis), glomerulonephritides, vasculitides (e.g., necrotizing, cutaneous, and hypersensitivity vasculitis), hepatitis, diabetes, systemic lupus erythematosus and myasthenia gravis.

In addition to psoriasis, other inflammatory dermatoses such as dermatitis, ecrema, atopic dermatitis, allergis contact dermatitis, urticaria and reparfusion injury may also be treated.

The data in the table show the MCP-receptor binding activity of representative pyrazolones of the present invention.

MCP-1 BINDING ASSAY

Membranes used in the MCP-1 binding assay were prepared from THP-1 cells (human monocytic cell line source—American Type Culture Collection, Tumor Immunology Bank #202, Rockville, Md., accession no. ATCC TIB 202) selected for increased levels of expression of the MCP-1 receptor. Cells were harvested by centrifugation and washed twice in ice-cold PBS (phosphate-buffered saline) and the cell pellet was frozen at $-80°$ C. in some cases. Cells were resuspended in ice-cold lysis buffer 5 mM HEPES (2-(4N-[2-hydroxyethyl] piperazin-1-yl)-N'-(2-ethanesulfonic acid), pH 7.5, 2 mM EDTA (ethylenediaminetetraacetic acid), 5 ug/ml each leupeptin, aprotinin, chymostatin (protease inhibitors), and 100 ug/ml PMSF (phenylmethane sulfonyl fluoride—also a protease inhibitor)) at a concentration of $5 \times 10^7$ cells/ml. The cell suspension was dounced 10–15 times using the B pestle (small pestle of tissue grinder—clearance is 0.07 mm; source—Fisher Scientific) on ice. Nuclei and debris were removed by centrifugation at 500–1000×g for 10 minutes at $4°$ C. The supernatant was transferred to a fresh tube and centrifuged at 25,000×g for 30 minutes at $4°$ C. The supernatant was aspirated and the pellet was resuspended in freezing buffer (10 mM HEPES, pH 7.5, 300 mM sucrose, 1 ug/ml each leupeptin, aprotinin, chymostatin, and 10 ug/ml PMSF) using a minihomogenizer until all clumps were resolved. Membranes were aliquoted and frozen at minus 70–85° C. until needed. Typical binding assays used 10–20 ug/well of total membrane protein as determined with a standard protein assay (e.g. BioRad, Richmond, Calif.) or:

as determined with a Bradford protein assay (e.g. BioRad, Richmond, Calif.).

For binding, different amounts of membranes were included in the binding reaction along with 0.2 nM $I^{125}$-labeled MCP-1 (Amersham, Arlington Heights, Ill.) with or without unlabeled cold competitor MCP-1 (Peprotech, Rocky Hill, N.J.) (at 500 nM). Binding reactions were performed in a final volume of 100 ul in a binding buffer containing 10 mM HEPES, pH 7.2, 1 mM $CaCl_2$, 5 mM $MgCl_2$, 0.5% BSA (bovine serum albumin). After 30 minutes at room temperature, the binding reactions were filtered through GF/C filters (Whatman glass fiber filters, Type C) or GF/B unifilter plates (Parkard) which had been pre-soaked with 0.3% poly ethyleneimine and washed twice with binding buffer containing 0.5 M NaCl. Filters were dried and counted in a Beta-Plate scintillation counter using standard scintillation fluid. Final concentration of compound in the binding assay ranged from 0.05–100 μM. Compounds were dissolved in DMSO (dimethyl sulfoxide). Final concentrations of DMSO in the binding were kept constant at 0.05%.

IC50s were calculated using a 3-parameter logistic fit. Negative control contained same amount of DMSO vehicle asused in wells containing compound. Positive control contained 500 nM cold competitor MCP-1 in DMSO vehicle.

TABLE 1

Some Compounds of the Invention

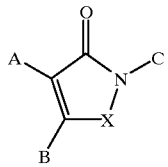

| EXAMPLE | C | X | A | B |
|---|---|---|---|---|
| 1 | H | NH | $NH_2$ | cyclohexyl |

TABLE 1-continued

Some Compounds of the Invention

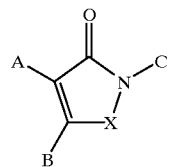

| EXAMPLE | C | X | A | B |
|---|---|---|---|---|
| 2 | H | NAc | NHAc | cyclohexyl |
| 3 | H | NH | $NH_2$ | -4-pyridyl |
| 4 | H | NH | $NH_2$ | Ph |
| 5 | H | $NCH_3$ | $NH_2$ | Ph |
| 6 | H | NH | $NH_2$ | 4-$OCH_3$ Ph |
| 7 | H | NH | NHCO Ph | H |
| 8 | H | NH | NHCO Ph | $CH_3$ |
| 9 | H | NH | $NH_2$ | H |
| 10 | H | NH | $NH_2$ | $CH_3$ |
| 11 | H | NH | $NH_2$ | $CF_3$ |
| 12 | H | NH | $NH_2$ | $(CH_2)_4 CH_3$ |
| 13 | Ph | $NCH_3$ | $NH_2$ | $CH_3$ |
| 14 | Ph | $NCH_3$ | $N(CH_3)_2$ | $CH_3$ |
| 15 | Ph | $NCH_3$ | N-(4-ethyl benzoate) | $CH_3$ |
| 16 | Ph | $NCH_3$ | -2,4-dinitro-aniline | $CH_3$ |
| 17 | Ph | $NCH_3$ | $NHCO_2Et$ | $CH_3$ |

TABLE II

Some N-Phenylpyrazoles of the invention

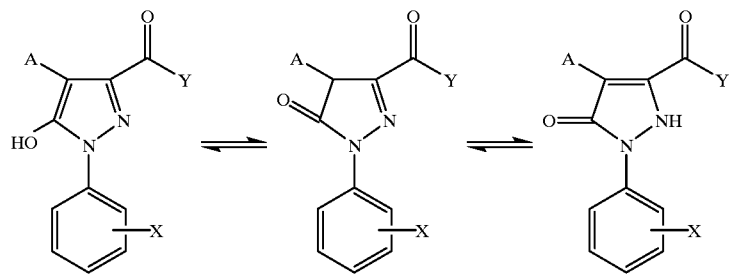

| EXAMPLE | A | Y | X |
|---|---|---|---|
| 18 | $NH_2$ | $NH_2$ | 2-Cl |
| 19 | $NH_2$ | $NH_2$ | 2,4-$Cl_2$ |
| 20 | $NH_2$ | $NH_2$ | 3,5-$Cl_2$ |
| 21 | $NH_2$ | $NH_2$ | 4-Cl |
| 22 | $NH_2$ | $NH_2$ | 2,5-$Cl_2$ |
| 23 | $NH_2$ | $NH_2$ | 3-Cl |
| 24 | $NHCOCO_2Et$ | $NH_2$ | H |
| 25 | $NH_2$ | $NH_2$ | $SO_2CH_3$ |
| 26 | $NH_2$ | $NH_2$ | 2,5-$Cl_2$ |
| 27 | $NH_2$ | $NH_2$ | 2,3-$Cl_2$ |

TABLE II-continued

Some N-Phenylpyrazoles of the invention

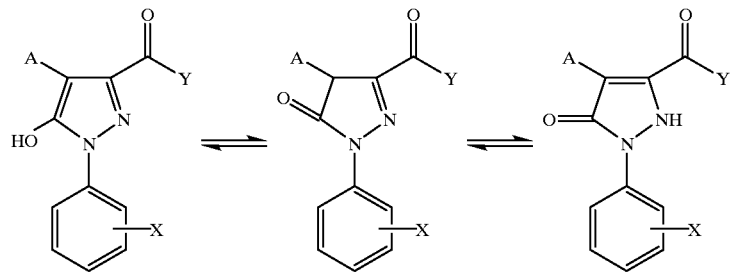

| EXAMPLE | A | Y | X |
|---|---|---|---|
| 28 | NHCOCH$_2$ CO$_2$Et | NH$_2$ | H |
| 29 | NH$_2$ | NH$_2$ | 3,4-Me$_2$ |
| 30 | NH$_2$ | NH$_2$ | H |
| 31 | NH$_2$ | OEt | H |

Preferred compounds are as follows:

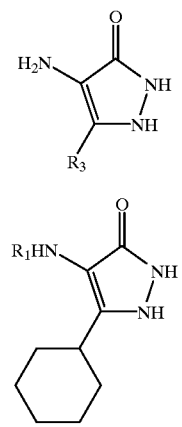

TABLE III

BIOLOGICAL ACTIVITY: MCP-1 BINDING ASSAY

| Ex | R$_1$ | R$_2$ | R$_3$ | R$_4$ | R$_5$ | Inhibition of MCP-1 Binding IC$_{50}$ μM |
|---|---|---|---|---|---|---|
| (1) | H | H | cyclohexyl | H | H | 1.27 |
| (3) | H | H | 4-pyridyl | H | H | 95% @ 10 μM |
| (4) | H | H | Ph | H | H | 0.73 |
| (5) | H | H | Ph | CH$_3$ | H | 90% @ 10 μM |
| (6) | H | H | 4-MeOPh | H | H | 1.49 |
| (9) | H | H | H | H | H | 1.65 |
| (13) | H | H | CH$_3$ | CH$_3$ | Ph | 2.27 |
| (37) | H | —CH$_2$CH$_2$CH$_2$— | H | H | 5.64 |

TABLE III-continued

BIOLOGICAL ACTIVITY: MCP-1 BINDING ASSAY

| Ex | R$_1$ | R$_2$ | R$_3$ | R$_4$ | R$_5$ | Inhibition of MCP-1 Binding IC$_{50}$ μM |
|---|---|---|---|---|---|---|
| (18) | H | H | CONH$_2$ | H | 4-ClPh | 6.28 |
| (19) | H | H | CONH$_2$ | H | 2,4-Cl$_2$Ph | 6.24 |

CD3—Blast Chemotaxis Assay

Recombinant human MCP-1 was obtained from Peprotech (Rockey Hill, N.J.). T lymphocyte blast cells (CD3-Blasts) were generated by standard protocols familiar to those skilled in the art (Coligan, J. E., A. M. Kruisbeek, D. H. Macgulies, E. M. Shevach, and W. Strober, editors. 1992. Current Protocols in Immunology. John Wiley and Sons, New York). Briefly, human peripheral blood mononuclear cells (PBMC) were isolated from heparinized venous blood by Percoll density gradient centrifugation (d=1.088) at room temperature. RBCs were removed by hypotonic lysis. Blast cells were generated by incubating 2×10$^6$ PBMC in 24-well tissue culture plates that were coated with 2.5 g of an anti-CD3 monoclonal antibody (identified as TR66, a gift from Dr. A. Lanzivecchia; similar monoclonal antibody is HIT3a, from Parmingen #30111A) at 37° C. for 48 to 72 hours, and then transferring 12-wells to T25 or T75 flasks with RPMI (Roswell Park memorial Institute 1640, a growth cell medium available from Gilco RBL, Inc., N.Y.)+10% FCS (fetal calf serum)+500/ml IL-2. The cells are expanded and cultured for up to 3 weeks. CD3-Blast chemotaxis was assessed no sooner than 3 to 4 days after transfer to the IL-2 containing medium using a modification of a transendothelial migration assay (Carr. M. W., S. J. Roth, B. Luther, S. S. Rose, and T. A. Springer. 1994. Monocyte chemoattractant protein 1 acts as a T-lymphocyte chemoattractant. Proc.

Natl. Acad. Sci. USA 91:3652–6). The endothelial cells used for this assay were the endothelial cell line ECV304, obtained from the ECACE (Porton Downs, UK). Endothelial cells were cultured on 6.5 mm diameter Transwell culture inserts (Costar) with a 3.0 mm pore size. Culture media for ECV304 cells (ECV304 was from the European Collection of Animal Cell Cultures assession #92091712) consisted of M199 (a cell culture medium from Gibco BRL, Inc., Gaithersburg, Md.)+10% FCS (fetal calf serum from Gibco BRL, Inc.), L-glutamine, and antibiotics (the penicillin concentration was 50 U/ml, and the streptomycin concentration was 50 ug/ml; both from Gibco, N.Y.). Assay media consisted of equal parts RPMI 1640 and M199, with 0.5% BSA (bovine serum albumin or simply RPMI 1640 with 0.5% BSA). Twenty four hours before the assay, $2 \times 10^5$ ECV304 cells were plated onto each innert of the 24 well chemotaxis plate and incubated at 37° C. MCP-1 (diluted in assay medium) with or without compounds, was added to the 24-well tissue culture plates in a final volume of 600 ml. Endothelial coated Transwells were inserted into each well and 106 leukocytes (source) were added to the top chamber in a final volume of 100 ml, with or without compounds. The plate was then incubated at 37° C. in 5% CO2/95% air for approximately 1 hour. The cells that had migrated to the bottom chamber were enumerated using flow cytommetry. 500 ml of the cell suspension from the lower chamber was placed in a tube, and relative cell counts were obtained by acquiring events for a set time period of 30 seconds. This counting method was found to be highly reproducible, and enabled gating on the leukocytes and the exclusion of debris or other cells. Background migration was determined by counting cells that migrated in the absence of MCP-1 in the lower chamber. This background migration of cells per 30 second count was substrated from the migration to MCP-1 to obtain specific migration. The percent inhibition by compounds of directed migration was determined by the following formula: 1 minus the specific migration in the presence of MCP-1 and compound, divided by the specific migration in the presence of just MCP-1.

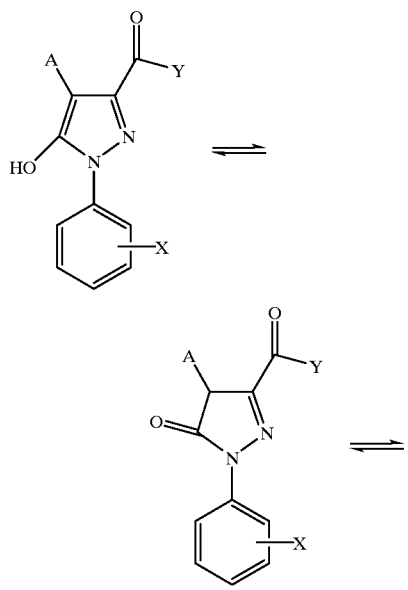

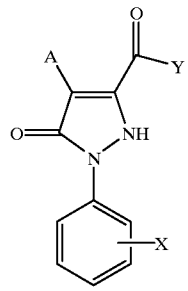

TABLE IV

INHIBITION OF MCP-1 MEDIATED CHEMOTAXIS ASSAY OF CD3-BLAST

| EX # | A | Y | X | IC$_{50}$ |
|---|---|---|---|---|
| 19 | NH$_2$ | NH$_2$ | 2,4-Cl$_2$ | 0.48 |

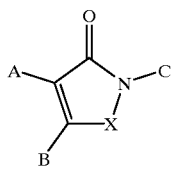

TABLE V

INHIBITION OF MCP-1 MEDIATED CHEMOTAXIS ASSAY OF CD3-BLAST

| EX # | C | X | A | B | % of Inhibition (10 μM)* |
|---|---|---|---|---|---|
| 1 | H | NH | NH$_2$ | cyclohexyl | 33–70 |
| 3 | H | NH | NH$_2$ | 4-pyridyl | 5–49 |
| 4 | H | NH | NH$_2$ | Ph | 58–61 |
| 10 | H | NH | NH$_2$ | CH$_3$ | 25–27 |
| 5 | H | NCH$_3$ | NH$_2$ | Ph | −23–48 |

*Range given for multiple replications

Streptococcal Cell Wall Arthritis

Figure 2:
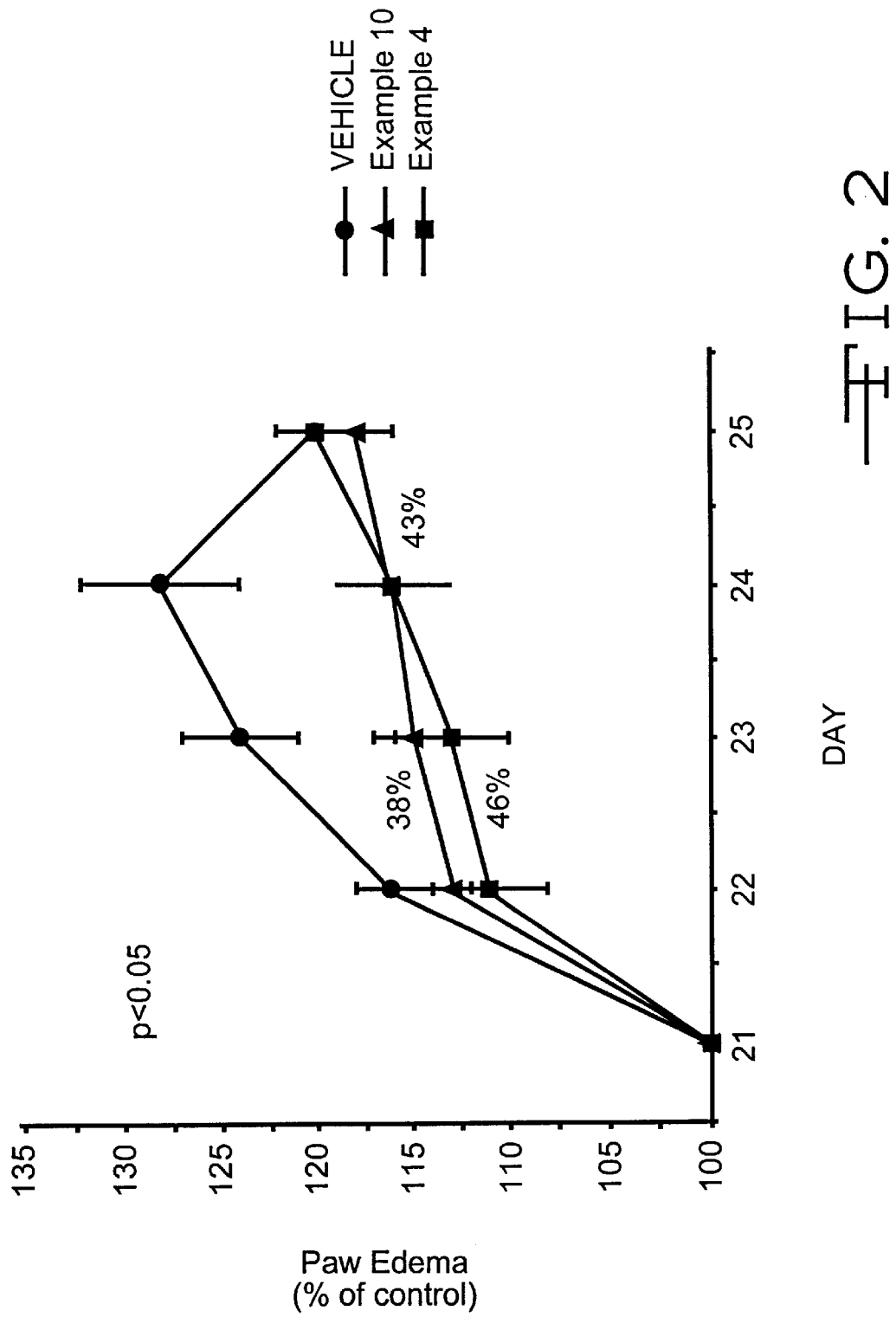

Streptococcal cell wall (SCW) arthritis was induced in female Lewis rats (200 gms). To induce the subacute, transient arthritic response, a highly refined preparation of streptococcal cell walls (100P, Lee Laboratories, Grayson, Ga.) was injected into the ankle joints of female Lewis rats (6 μl/rat in Dulbecco's PBS). Twenty one days later, the animals were given an IV booster of SCW at a dose of 100 μg/rat in 0.25 mL of Dulbecco's PBS. Vehicle (0.5% hydroxypropylmethylcellulose and 0.2% Tween 80, 10 mL/kg) or test compounds suspended in vehicle were given one hour before the IV challenge with SCW and daily thereafter for 3 additional days. Paw volume was measured daily by mercury plethysmography. Swelling was determined by comparing paw volume at the various timepoints with an initial paw volume measurement for each rat. Percent inhibition of swelling in compound-treated rats was determined in comparison with swelling rats treated with vehicle. Statistical power was calculated using an analysis of covariance with a contrast mean comparison test (n=5–10 per experimental group). See test results in FIGS. 1–2 for examples 4 and 10 (FIG. 2) and example 1 (FIG. 1).

The compounds of the present invention can be prepared and administered in a wide variety of routes of administration such as parenteral, oral, topical, rectal, inhalation and the like. Formulations will vary according to the route of administration selected. Examples are oral and parenteral dosage forms. Thus, the compounds of the present invention can be administered by injection, that is, intravenously, intramuscularly, intra-cutaneously, subcutaneously, intraduodenally, or intraperitoneally. Also, the compounds of the present invention can be administered by inhalation, for example, intranasally. Additionally, the compounds of the present invention can be administered transdermally. The following dosage forms may comprise as the active component, a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or-more substances which may also act as diluents, flavoring agents, binders, preservatives, tablet disintegrating agents, or an encapsulating material.

In powders, the carrier can be a finely divided solid which is in a mixture with the finely divided active component.

In tablets, the active component can be mixed with the carrier having the necessary binding properties in suitable proportions and compacted in the shape and size desired.

The powders and tablets preferably contain from 5% or 10% to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component can be dispersed homogeneously therein, as by stirring. The molten homogenous mixture can be then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted for example from about 0.1 mg to 200 mg, preferably about 0.5 mg to 100 mg according to the particular application and the potency of the active component. The composition can, if desired, also contain other compatible therapeutic agents.

In therapeutic use as agents for the treatment of atherosclerosis, restenosis, and immune disorders such as arthritis and transplant rejection, the compounds utilized in the pharmaceutical methods of this invention can be administered at an initial dosage of about 0.01 mg to about 200 mg/kg daily. A daily dose range of about 0.01 mg to about 50 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The ACAT inhibitors, HMG-CoA reductase inhibitors, lipid regulators, and bile acid sequestrants utilized in the second embodiment of the present invention can be used in standard dosage amounts known in the art.

As further exemplification of the invention listed below are preferred embodiments wherein all parts are parts by weight and all temperatures are degrees Centigrade unless otherwise indicated.

Examples of preferred-compounds are:

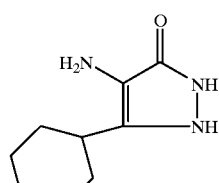

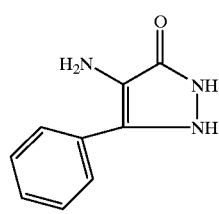

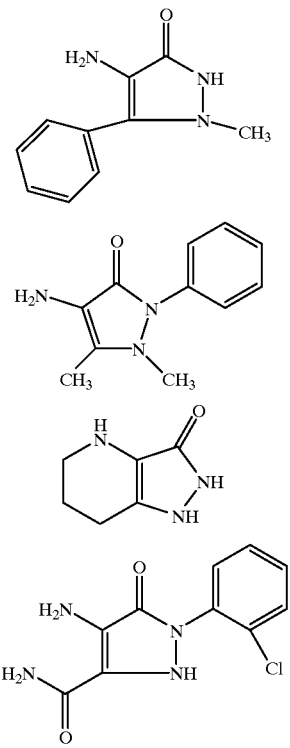

EXAMPLE 1
Pyrazolone Derivative (Example 1; 4-Amino 5-Cyclohexyl-3-Pyrazolone) Inhibits T-Cell Recruitment To Rat Skin Inflammatory Sites Method of Evaluation Inbred, approximately 200 gm, male Lewis rats were used in all experiments. Cutaneous delayed hypersensitivity (DHR) was induced as previously described (1). Briefly, rats were sensitized to KLH (keyhole limpet hemocyanis) (Sigma Chemical Co., St. Louis, Mo.) by administering 50 $\mu$g KLH in 0.1 ml complete Freund's adjuvant (CFA; Sigma Chemical Co.) into each of 4 subcutaneous sites. After 14 days, DHR was elicited by the challenge of 5 $\mu$g KLH in PBS into multiple intradermal sites on the back. Analysis was performed 24 hours after antigen challenge. For each experiment, there were at least three groups of animals of at least four animals in each group. One group of nonsensitized, naive animals was used as a negative control and received vehicle alone (consisting of 0.5% hydroxypropylmethylcellulose/0.2% Tween 80 in water) per os at the time of challenge. As positive controls, one group of sensitized animals received vehicle alone per os at the time of KLH challenge. A third group consisted of sensitized animals that received compound suspended in vehicle per os at the time of KLH challenge.

T cell recruitment at sites of DHR was quantified using methods previously described (1–4). Briefly, rat T cells were isolated from spleen of naive adult Lewis rats by mincing the splenic tissue, removing the red cells by hypotonic lysis, and passing the cells through a nylon wool column. The cells in the effluent were highly purified (>95%) rat T cells as assessed by anti-rat CD3 (monoclonal antibody KT3, Biosource International, Camarillo, Calif.) immunoreactivity by flow cytometry. Radiolabeling was performed by suspending $5\times10^7$ T cells in 0.5 ml RPMI 1640 medium with 7.5 $\mu$Ci $^{111}$In-oxiquinoline (Amersharp Corp., Arlington Heights, Ill.) for 20 minutes at room temperature so that $2\times10^7$ T cells yielded approximately $0.5-2\times10^6$ cpm of $\gamma$ activity. The cells were then washed twice, reaspended in RPMI 1640 plus 10% normal rat serum, and $2\times10^7$ labeled T cells/200 gm body weight rat were injected intravenously at the time of KLH intradermal challenge. Skin challenge sites (8 mm in diameter) were counted on a $\gamma$ counter 24 hours after injection of radiolabeled T cells. Lung, liver, and spleen were also collected and counted as comparative indices for evaluation of input.

For histologic analysis, representative skin specimens were fixed in 10% phosphate-buffered formalin, processed by routine histological techniques, cut at a thickness of 6.0 AM, and sections stained with hematoxylin and eosin.

Statistical significance was determined using a paired student's t-test. Differences between means were considered significant when P<0.05.

Results

Figure 3:
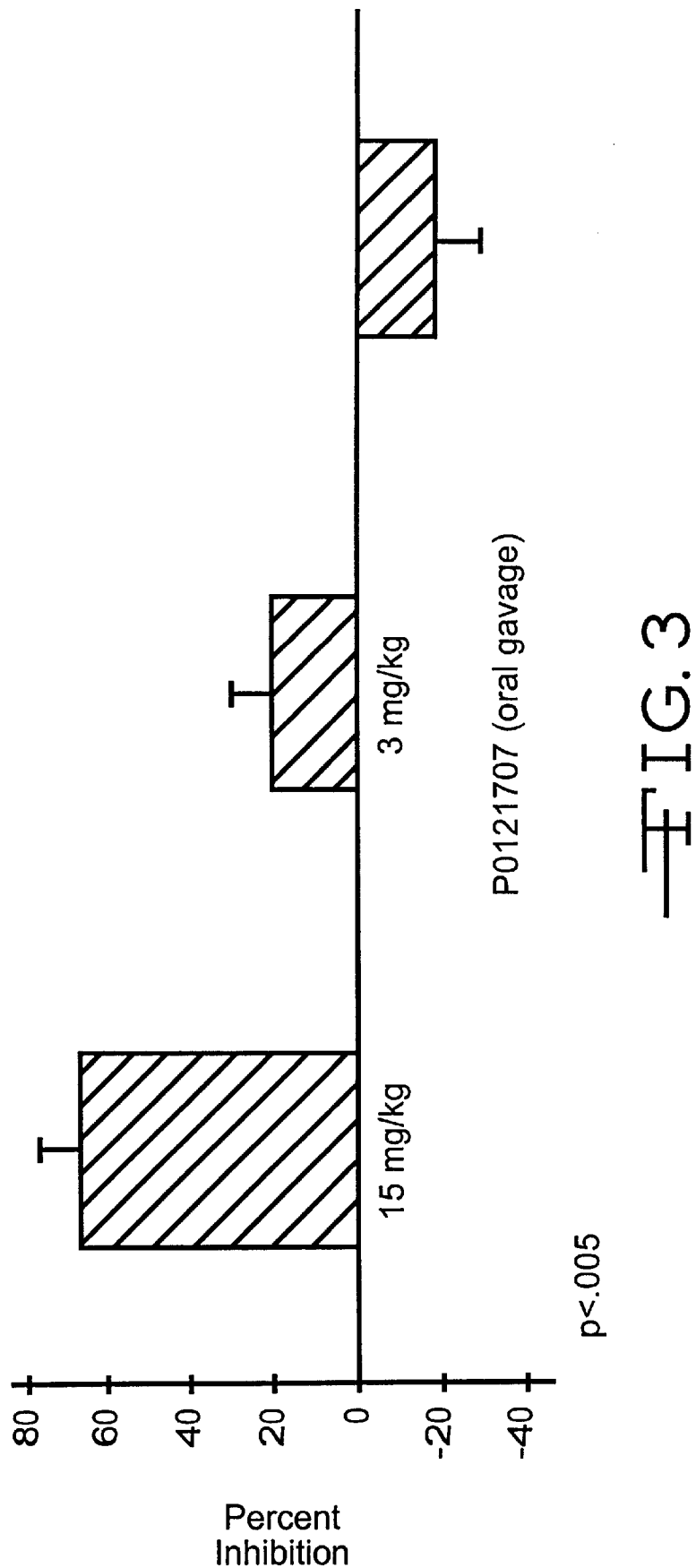
FIG. 3 is a graphic illustration of the degree of inhibition of T cell recruitment in rat delayed hypersensitivity (DHR) over a 24 hour period at various doses of example 1.

When administered once per os at the time of antigen challenge, Example 1 inhibited the recruitment of $^{111}$In-labeled rat T cells to skin DHR sites in a dose-dependent fashion (FIG. 3). Furthermore, when examined histologically, skin sites from animals administered compound at 15 mg/kg were attenuated in inflammatory activity and characterized by reduced mononuclear cells infiltration in deep dermis when compared to skin samples from senstized animals given vehicle alone.

Brief Description of the Drawings

FIG. 3 is a graphic illustration of the degree of inhibition of T cell recruitment in rat DHR over a 24 hour period at various doses of Example 1. There was a statistically significant inhibitory effect of the compound when administered at 15 mg/kg per os at the time of antigen challenge.

REFERENCES

1. Issekutz, T. B., J. M. Stoltz, and P. V. D. Meide, 1988, Lymphocyte recruitment in delayed-type hypersensitivity: the role of IPN-$\gamma$, J. Immunol. 140:2989–2993.
2. Issetkutz, T. B. 1991, Inhibition of in vivo lymphocyte migration to inflammation and homing to lymphoid tissues by the TA-2 monoclonal antibody: a likely role for VLA-4 in vivo, J. Immunol., 147:4178–4184.
3. Issekutz, T. B. and A. C. Issekutz, 1991. T lymphocyte migration to arthritic joints and dermal inflammation in the rat: differing migration patterns and the involvement of VLA-4, Clin. Immunol. Immunopathol. 61:436–447.
4. Issekutz, T. B. 1993, Dual inhibition of VLA-4 and LFA-1 maximally inhibits cutaneous delayed-type hypersensitivity-induced inflammation. Am. J. Pathol. 143:1286–1293.

While the forms of the invention herein disclosed constitute presently preferred embodiments, many others are possible. It is not intended herein to mention all of the possible equivalent forms or ramifications of the invention. It is understood that the terms used herein are merely descriptive rather than limiting and that various changes may be made without departing from the spirit or scope of the invention.

What is claimed is:

1. A compound of Formula I

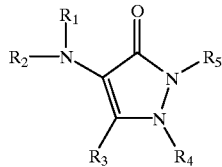

FORMULA I where: $R_1$, $R_2$ can be independently
H,
$C_{1-20}$ alkyl,
$C_{5-7}$ cycloalkyl,
—$(CH_2)_n NR_6 R_7$
—$(CH_2)_{0-6} CONR_6 R_7$,
—$(CH_2)_n OH$,
—$(CH_2)0-6CO_2 R_{11}$;
biphenyl,
aryl of from 6 to 10 carbon atoms, or
aryl of from 6 to 10 carbon atoms substituted up to 3 times by halogen, —CN, lower alkyl of from 1–4 carbon atoms, —OH, nitro, —$SO_2H$, —$SO_2$ lower alkyl,
—$SO_2 NR_6 R_7$, lower alkoxy,
—$CO_2 R_{11}$,
—$CONR_6 R_7$,
—$NR_6 R_7$, or
—$CH_2 OH$;
wherein n is an integer from 0–6 providing n is not 1 when the moiety is $R_1$, $R_2$, $R_4$ and/or $R_5$ and n can not be 0 when the moiety is $R_4$ or $R_5$;
$R_6$ and $R_7$ can be independently
H, lower alkyl of from 1–4 carbon atoms, or
$(CH_2)_n NR_8 R_9$;
$R_8$ and $R_9$ can independently by H or lower alkyl;
$R_{10}$ is H, alkyl of from 1–4 carbon atoms, $(CH_2)_n Ph$, or $(CH_2)_n CHPH_2$ where "Ph" is phenyl;
$R_{11}$ is H or lower alkyl of from 1–4 carbon atoms;
$R_2$ and $R_3$ or $R_3$ and $R_4$ or $R_4$ and $R_5$ can independently be taken together to form a ring of 5–7 atoms;
further either one of $R_1$ or $R_2$ can independently be
—$C(O)R_{12}$,
—$C(S)R_{12}$ or,
—$CO_2 R_{12}$,
where $R_{12}$ is lower alkyl of from 1–4 carbon atoms, phenyl or phenyl substituted up to 3 times with substituents as previously defined above;
$R_3$ is —$C(O)NH(CH_2)_n NR_6 R_7$,
$R_4$ can be independently H, or $C_{1-20}$alkyl;
$R_5$ can be independently H, $C_{1-20}$ alkyl, $C_{5-7}$ cycloalkyl;
aryl of from 6 to 10 carbon atoms, or
aryl of from 6 to 10 carbon atoms substituted up to 3 times by halogen, —CN, lower alkyl of from 1–4 carbon atoms, —OH, nitro, —$SO_2H$, —$SO_2$ lower alkyl,
—$SO_2 NR_6 R_7$, lower alkoxy,
—$CO_2 R_{11}$,
—$CONR_6 R_7$,
—$NR_6 R_7$, or
—$CH_2 OH$.

2. A method for the treatment of inflammatory disease or condition, atherosclerosis, restenosis, chronic or acute immune disorders, and transplant rejection in a mammal in need thereof comprising administering to such mammal an effective amount of a compound of Formula I

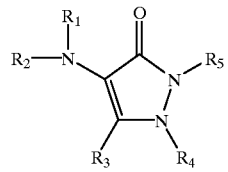

FORMULA I where: $R_1$, $R_2$ can be independently
H,
$C_{1-20}$ alkyl,
$C_{5-7}$ cycloalkyl,
—$(CH_2)_n NR_6 R_7$
—$(CH_2)_{0-6} CONR_7$,
—$(CH_2)_n OH$,
—$(CH_2)_{0-6} CO_2 R_{11}$;
biphenyl,
aryl of from 6 to 10 carbon atoms, or
aryl of from 6 to 10 carbon atoms substituted up to 3 times by halogen, —CN, lower alkyl of from 1–4 carbon atoms, —OH, nitro, —$SO_2H$, —$SO_2$ lower alkyl,
—$SO_2 NR_6 R_7$, lower alkoxy,
—$CO_2 R_{11}$,
—$CONR_6 R_7$,
—$NR_6 R_7$, or
—$CH_2 OH$;
wherein n is an integer from 0–6 providing n is not 1 when the moiety is $R_1$, $R_2$, $R_4$ and/or $R_5$ and n can not be 0 when the moiety is $R_4$ or $R_5$;
$R_6$ and $R_7$ can be independently
H, lower alkyl of from 1–4 carbon atoms, or
$(CH_2)_n NR_8 R_9$;
$R_8$ and $R_9$ can independently by H or lower alkyl;
$R_{10}$ is H, alkyl of from 1–4 carbon atoms, $(CH_2)_n Ph$, or $(CH_2)_n CHPH_2$ where "Ph" is phenyl;
$R_{11}$ is H or lower alkyl of from 1–4 carbon atoms;
$R_2$ and $R_3$ or $R_3$ and $R_4$ or $R_4$ and $R_5$ can independently be taken together to form a ring of 5–7 atoms;
further either one of $R_1$ or $R_2$ can independently be
—$C(O)R_{12}$,
—$C(S)R_{12}$ or,
—$CO_2 R_{12}$,
where $R_{12}$ is lower alkyl of from 1–4 carbon atoms, phenyl or phenyl substituted up to 3 times with substituents as previously defined above;
where $R_3$ can be
H,
$C_{1-20}$ alkyl,
$C_{5-7}$ cycloalkyl,
—$(CH_2)_n NR_6 R_7$
—$(CH_2)_{0-6} CONR_6 R_7$,
—$(CH_2)_n OH$,
—$(CH_2)_{0-6} CO_2 R_{11}$;
—$CF_3$;
biphenyl,
aryl of from 6 to 10 carbon atoms, or aryl of from 6 to 10 carbon atoms substituted up to 3 times
by halogen, —CN, lower alkyl of
from 1–4 carbon atoms, —OH, nitro, —SO$_2$H, —SO$_2$
lower alkyl,
—SO$_2$NR$_6$R$_7$,
lower alkoxy,
—CO$_2$R$_{11}$,
—CONR$_6$R$_7$,
—NR$_6$R$_7$, or
—CH$_2$OH;
R$_4$ can be independently H, or C$_{1-20}$ alkyl;
R$_5$ can be independently H, C$_{1-20}$ alkyl, C$_{5-7}$ cycloalkyl;
aryl of from 6 to 10 carbon atoms, or
aryl of from 6 to 10 carbon atoms substituted up to 3 times
by halogen, —CN, lower alkyl of
from 1–4 carbon atoms, —OH, nitro, —SO$_2$H, —SO$_2$
lower alkyl,
—SO$_2$NR$_6$R$_7$, lower alkoxy,
—CO$_2$R$_{11}$,
—CONR$_6$R$_7$,
—NR$_6$R$_7$, or
—CH$_2$OH.

3. A method for the treatment of atherosclerosis in a mammal in need thereof comprising administering to such mammal an effective amount of a compound of Formula I

FORMULA I

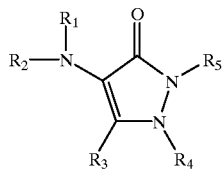

where: R$_1$, R$_2$ can be independently
H,
C$_{1-20}$ alkyl,
C$_{5-7}$ cycloalkyl,
—(CH$_2$)$_n$NR$_6$R$_7$
—(CH$_2$)$_{0-6}$CONR$_6$R$_7$,
—(CH$_2$)$_n$OH,
—(CH$_2$)$_{0-6}$CO$_2$R$_{11}$;
biphenyl,
aryl of from 6 to 10 carbon atoms, or
aryl of from 6 to 10 carbon atoms substituted up to 3 times
by halogen, —CN, lower alkyl of
from 1–4 carbon atoms, —OH, nitro, —SO$_2$H, —SO$_2$
lower alkyl,
—SO$_2$NR$_6$R$_7$, lower alkoxy,
—CO$_2$R$_{11}$,
—CONR6R$_7$,
—NR$_6$R$_7$, or
—CH$_2$OH;
wherein n is an integer from 0–6 providing n is not 1 when
the moiety is R$_1$, R$_2$, R$_4$ and/or R$_5$ and n can not be 0 when
the moiety is R$_4$ or R$_5$;
R$_6$ and R$_7$ can be independently
H, lower alkyl of from 1–4 carbon atoms, or
(CH$_2$)$_n$NR$_8$R$_9$;
R$_8$ and R$_9$ can be independently by H or lower alkyl;
R$_{10}$ is H, alkyl of from 1–4 carbon atoms, (CH$_2$)$_n$Ph, or
(CH$_2$)$_n$CHPH$_2$ where "Ph" is phenyl;

R$_{11}$ is H or lower alkyl of from 1–4 carbon atoms;
R$_2$ and R$_3$ or R$_3$ and R$_4$ or R$_4$ and R$_5$ can independently be
taken together to form a ring of 5–7 atoms;
further either one of R$_1$ or R$_2$ can independently be
—C(O)R$_{12}$,
—C(S)R$_{12}$ or,
—CO$_2$R$_{12}$,
where R$_{12}$ is lower alkyl of from 1–4 carbon atoms, phenyl
or phenyl substituted up to 3 times with substituents as
previously defined above;
where R$_3$ can be
H,
C$_{1-20}$ alkyl,
C$_{5-7}$ cycloalkyl,
—(CH$_2$)$_n$NR$_6$R$_7$
—(CH$_2$)$_{0-6}$CONR$_6$R$_7$,
—(CH2)$_n$OH,
—(CH$_2$)$_{0-6}$CO$_2$R$_{11}$;
—CF$_3$;
biphenyl,
aryl of from 6 to 10 carbon atoms, or
aryl of from 6 to 10 carbon atoms substituted up to 3 times
by halogen, —CN, lower alkyl of
from 1–4 carbon atoms, —OH, nitro, —SO$_2$H, —SO$_2$
lower alkyl,
—SO$_2$NR$_6$R$_7$,
lower alkoxy,
—CO$_2$R$_{11}$,
—CONR$_6$R$_7$,
—NR$_6$R$_7$, or
—CH$_2$OH;
R$_4$ can be independently H, or C$_{1-20}$ alkyl;
R$_5$ can be independently H, C$_{1-20}$ alkyl, C$_{5-7}$ cycloalkyl;
aryl of from 6 to 10 carbon atoms, or
aryl of from 6 to 10 carbon atoms substituted up to 3 times
by halogen, —CN, lower alkyl of
from 1–4 carbon atoms, —OH, nitro, —SO$_2$H, —SO$_2$
lower alkyl,
—SO$_2$NR$_6$R$_7$, lower alkoxy,
—CO$_2$R$_{11}$,
—CONR$_6$R$_7$,
—NR$_6$R$_7$, or
—CH$_2$OH.

4. A method of treating inflammation in a mammal in need thereof comprising administrating to such mammal an effective anti-inflammatory a mount of a compound of Formula I

FORMULA I

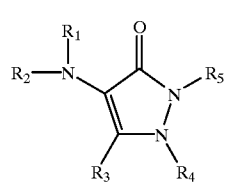

where: R$_1$, R$_2$ can be independently
H,
C$_{1-20}$ alkyl,
C$_{5-7}$ cycloalkyl,
—(CH$_2$)$_n$NR$_6$R$_7$
—(CH$_2$)$_{0-6}$CONR$_6$R$_7$, —(CH$_2$)$_n$OH,
—(CH$_2$)$_{0-6}$CO$_2$R$_{11}$;
biphenyl,
aryl of from 6 to 10 carbon atoms, or
aryl of from 6 to 10 carbon atoms substituted up to 3 times by halogen, —CN, lower alkyl of
from 1–4 carbon atoms, —OH, nitro, —SO$_2$H, —SO$_2$ lower alkyl,
—SO$_2$NR$_6$R$_7$, lower alkoxy,
—CO$_2$R$_{11}$,
—CONR$_6$R$_7$,
—NR$_6$R$_7$, or
—CH$_2$OH;
wherein n is an integer from 0–6 providing n is not 1 when the moiety is R$_1$, R$_2$, R$_4$ and/or R$_5$ and n can not be 0 when the moiety is R$_4$ or R$_5$;
R$_6$ and R$_7$ can be independently
H, lower alkyl of from 1–4 carbon atoms, or
(CH$_2$)$_n$NR$_8$R$_9$;
R$_8$ and R$_9$ can independently by H or lower alkyl;
R$_{10}$ is H, alkyl of from 1–4 carbon atoms, (CH$_2$)$_n$Ph, or (CH$_2$)$_n$CHPH$_2$ where "Ph" is phenyl;
R$_{11}$ is H or lower alkyl of from 1–4 carbon atoms;
R$_2$ and R$_3$ or R$_3$ and R$_4$ or R$_4$ and R$_5$ can independently be taken together to form a ring of 5–7 atoms;
further either one of R$_1$ or R$_2$ can independently be
—C(O)R$_{12}$,
—C(S)R$_{12}$ or,
—CO$_2$R$_{12}$,
where R$_{12}$ is lower alkyl of from 1–4 carbon atoms, phenyl or phenyl substituted up to 3 times with substituents as previously defined above;
where R$_3$ can be
H,
C$_{1-20}$ alkyl,
C$_{5-7}$ cycloalkyl,
—(CH$_2$)$_n$NR$_6$R$_7$
—(CH$_2$)$_{0-6}$CONR$_6$R$_7$,
—(CH$_2$)$_n$OH,
—(CH$_2$)$_{0-6}$CO$_2$R$_{11}$;
—CF$_3$;
biphenyl,
aryl of from 6 to 10 carbon atoms, or
aryl of from 6 to 10 carbon atoms substituted up to 3 times by halogen, —CN, lower alkyl of
from 1–4 carbon atoms, —OH, nitro, —SO$_2$H, —SO$_2$ lower alkyl,
—SO$_2$NR$_6$R$_7$,
lower alkoxy,
—CO$_2$R$_{11}$,
—CONR$_6$R$_7$,
—NR$_6$R$_7$, or
—CH$_2$OH;
R$_4$ can be independently H, or C$_{1-20}$ alkyl;
R$_5$ can be independently H, C$_{1-20}$ alkyl, C$_{5-7}$ cycloalkyl;
aryl of from 6 to 10 carbon atoms, or
aryl of from 6 to 10 carbon atoms substituted up to 3 times by halogen, —CN, lower alkyl of
from 1–4 carbon atoms, —OH, nitro, —SO$_2$H, —SO$_2$ lower alkyl,
—SO$_2$NR$_6$R$_7$, lower alkoxy,
—CO$_2$R$_{11}$,
—CONR$_6$R$_7$,
—NR$_6$R$_7$, or
—CH$_2$OH.

5. The method of claim 2, wherein in a compound of Formula I, R$_3$ is hydrogen, alkyl, cycloalkyl or phenyl.

6. The method of claim 2 wherein R$_1$ and R$_2$ are hydrogen.

7. The method of claim 2 wherein R$_5$ is phenyl or substituted phenyl.

8. The method of claim 2 wherein the Formula I compound is selected from the group consisting of Formula A and Formula B:

FORMULA A

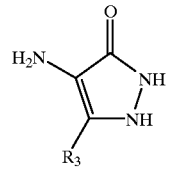

FORMULA B

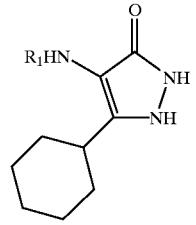

9. The method of claim 4 wherein the inflammation is associated with lymphocyte or monocyte recruitment or accumulation.

10. The method of claim 4 wherein R$_3$ is hydrogen, methyl, cycloalkyl or phenyl.

11. The method of claim 4 wherein R$_4$ and R$_5$ are hydrogen.

12. The method of claim 4 wherein R$_5$ is mono- or di-substituted phenyl.

13. A pharmaceutical composition for the treatment of inflammation, atherosclerosis, restenosis, immune disorders and transplant rejection in a mammal in need thereof comprising administering to such mammal a therapeutically effective amount of a compound of Formula I in combination in admixture with a pharmaceutically acceptable excipient, diluent, or carrier

FORMULA I

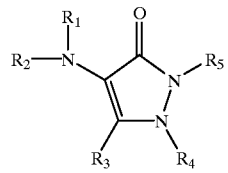

where: R$_1$, R$_2$ can be independently
H,
C$_{1-20}$ alkyl,
C$_{5-7}$ cycloalkyl,
—(CH$_2$)$_n$NR$_6$R$_7$
—(CH$_2$)$_{0-6}$CONR$_6$R$_7$,
—(CH$_2$)$_n$OH,
—(CH$_2$)$_{0-6}$CO$_2$R$_{11}$;
biphenyl, aryl of from 6 to 10 carbon atoms, or
aryl of from 6 to 10 carbon atoms substituted up to 3 times
by halogen, —CN, lower alkyl of
from 1–4 carbon atoms, —OH, nitro, —SO$_2$H, —SO$_2$
lower alkyl,
—SO$_2$NR$_6$R$_7$, lower alkoxy,
—CO$_2$R$_{11}$,
—CONR$_6$R$_7$,
—NR$_6$R$_7$, or
—CH$_2$OH;
wherein n is an integer from 0–6 providing n is not 1 when
he moiety is R$_1$, R$_2$, R$_4$ and/or R$_5$ and n can not be 0 when
the moiety is R$_4$ or R$_5$;
R$_6$ and R$_7$ can be independently
H, lower alkyl of from 1–4 carbon atoms, or
(CH$_2$)$_n$NR$_8$R$_9$;
R$_1$ and R$_9$ can independently by H or lower alkyl;
R$_{10}$ is H, alkyl of from 1–4 carbon atoms, (CH$_2$)$_n$Ph, or
(CH$_2$)$_n$CHPH$_2$ where "Ph" is phenyl;
R$_{11}$ is H or lower alkyl of from 1–4 carbon atoms;
R$_2$ and R$_3$ or R$_3$ and R$_4$ or R$_4$ and R$_5$ can independently be
taken together to form a ring of 5–7 atoms;
further either one of R$_1$ or R$_2$ can independently be
—C(O)R$_{12}$,
—C(S)R$_{12}$ or,
—CO$_2$R$_{12}$,
where R$_{12}$ is lower alkyl of from 1–4 carbon atoms, phenyl
or phenyl substituted up to 3 times with substituents as
previously defined above;
where R$_3$ can be
H,
C$_{1-20}$ alkyl,
C$_{5-7}$ cycloalkyl,
—(CH$_2$)$_n$NR$_6$R$_7$
—(CH$_2$)$_{0-6}$CONR$_6$R$_7$,
—(CH$_2$)$_n$OH,
—(CH$_2$)$_{0-6}$CO$_2$R$_{11}$;
—CF$_3$;
biphenyl,
aryl of from 6 to 10 carbon atoms, or
aryl of from 6 to 10 carbon atoms substituted up to 3 times
by halogen, —CN, lower alkyl of
from 1–4 carbon atoms, —OH, nitro, —SO$_2$H, —SO$_2$
lower alkyl,
—SO$_2$NR$_6$R$_7$,
lower alkoxy,
—CO$_2$R$_{11}$,
—CONR$_6$R$_7$,
—NR$_6$R$_7$, or
—CH$_2$OH;
R$_4$ can be independently H, or C$_{1-20}$ alkyl;
R$_5$ can be independently H, C$_{1-20}$ alkyl, C$_{5-7}$ cycloalkyl;
aryl of from 6 to 10 carbon atoms, or
aryl of from 6 to 10 carbon atoms substituted up to 3 times
by halogen, —CN, lower alkyl of
from 1–4 carbon atoms, —OH, nitro, —SO$_2$H, —SO$_2$
lower alkyl,
—SO$_2$NR$_6$R$_7$, lower alkoxy,
—CO$_2$R$_{11}$,
—CONR$_6$R$_7$,
—NR$_6$R$_7$, or
—CH$_2$OH.
14. The composition of claim 13 comprising the compound recited below:

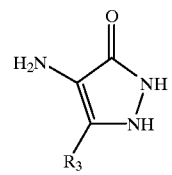

15. The composition of claim 13 comprising the compound recited below:

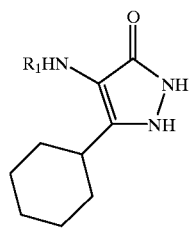

16. The composition of claim 13 wherein R$_1$, R$_4$ and R$_5$ are hydrogen and R$_3$ is phenyl.
17. A method of inhibiting the binding of the MCP-1 receptor in a mammal in need thereof comprising administrating to such mammal an effective inhibiting amount of a compound of Formula I

FORMULA I

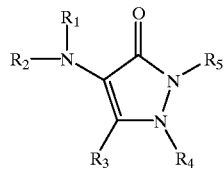

where: R$_1$, R$_2$ can be independently
H,
C$_{1-20}$ alkyl,
C$_{5-7}$ cycloalkyl,
—(CH$_2$)$_n$NP$_6$R$_7$
—(CH$_2$)$_{0-6}$CONR$_6$R$_7$,
—(CH$_2$)$_n$OH,
—(CH$_2$)$_{0-6}$CO$_2$R$_{11}$;
biphenyl,
aryl of from 6 to 10 carbon atoms, or
aryl of from 6 to 10 carbon atoms substituted up to 3 times
by halogen, —CN, lower alkyl of
from 1–4 carbon atoms, —OH, nitro, —SO$_2$H, —SO$_2$
lower alkyl,
—SO$_2$NR$_6$R$_7$, lower alkoxy,
—CO$_2$R$_{11}$,
—CONR$_6$R$_7$,
—NR$_6$R$_7$, or
—CH$_2$OH;
wherein n is an integer from 0–6 providing n is not 1 when
the moiety is R$_1$, R$_2$, R$_4$ and/or R$_5$ and n can not be 0 when
the moiety is R$_4$ or R$_5$;
R$_6$ and R$_7$ can be independently
H, lower alkyl of from 1–4 carbon atoms, or
(CH$_2$)$_n$NR$_8$R$_9$;
R$_8$ and R$_9$ can independently by H or lower alkyl;
R$_{10}$ is H, alkyl of from 1–4 carbon atoms, (CH$_2$)$_n$Ph, or
(CH$_2$)$_n$CHPH$_2$ where "Ph" is phenyl;

$R_{11}$ is H or lower alkyl of from 1–4 carbon atoms;

$R_2$ and $R_3$ or $R_3$ and $R_4$ or $R_4$ and $R_5$ can independently be taken together to form a ring of 5–7 atoms;

further either one of $R_1$ or $R_2$ can independently be

—C(O)$R_{12}$,
—C(S)$R_{12}$ or,
—CO$_2R_{12}$, where $R_{12}$ is lower alkyl of from 1–4 carbon atoms, phenyl or phenyl substituted up to 3 times with substituents as previously defined above;

where $R_3$ can be

H,
$C_{1-20}$ alkyl,
$C_{5-7}$ cycloalkyl,
—(CH$_2$)$_n$NR$_6$R$_7$
—(CH$_2$)$_{0-6}$CONR$_6$R$_7$,
—(CH$_2$)$_n$OH,
—(CH$_2$)0–6CO$_2R_{11}$;
—CF$_3$;
biphenyl,
aryl of from 6 to 10 carbon atoms, or
aryl of from 6 to 10 carbon atoms substituted up to 3 times by halogen, —CN, lower alkyl of from 1–4 carbon atoms, —OH, nitro, —SO$_2$H, —SO$_2$ lower alkyl,
—SO$_2$NR$_6$R$_7$,
lower alkoxy,
—CO$_2R_{11}$,
—CONR$_6$R$_7$,
—NR6R$_7$, or
—CH$_2$OH;

$R_4$ can be independently H, or $C_{1-20}$ alkyl;

$R_5$ can be independently H, $C_{1-20}$ alkyl, $C_{5-7}$ cycloalkyl;

aryl of from 6 to 10 carbon atoms, or aryl of from 6 to 10 carbon atoms substituted up to 3 times by halogen, —CN, lower alkyl of from 1–4 carbon atoms, —OH, nitro, —SO$_2$H, —SO$_2$ lower alkyl,
—SO$_2$NR$_6$R$_7$, lower alkoxy,
—CO$_2R_{11}$,
—CONR$_6$R$_7$,
—NR$_6$R$_7$, or
—CH$_2$OH.

18. The method of claim 2 wherein $R_1$ and $R_2$ are selected from the group consisting of hydrogen, $C_{1-20}$ alkyl, $C_{5-7}$ cycloalkyl, biphenyl and aryl of from 6–10 carbon atoms substituted or unsubstituted; $R_4$ and $R_5$ are hydrogen.

* * * * *